US009878045B2

(12) United States Patent
Distefano et al.

(10) Patent No.: US 9,878,045 B2
(45) Date of Patent: Jan. 30, 2018

(54) TRIORTHOGONAL REAGENTS FOR DUAL PROTEIN CONJUGATION

(71) Applicant: REGENTS OF THE UNIVERSITY OF MINNESOTA, Minneapolis, MN (US)

(72) Inventors: Mark Distefano, Minneapolis, MN (US); Mohammad Rashidian, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 15/029,599

(22) PCT Filed: Oct. 15, 2014

(86) PCT No.: PCT/US2014/060735
§ 371 (c)(1),
(2) Date: Apr. 14, 2016

(87) PCT Pub. No.: WO2015/057863
PCT Pub. Date: Apr. 23, 2015

(65) Prior Publication Data
US 2016/0271261 A1 Sep. 22, 2016

Related U.S. Application Data

(60) Provisional application No. 61/891,262, filed on Oct. 15, 2013.

(51) Int. Cl.
*A61K 47/55* (2017.01)
*A61K 47/62* (2017.01)
*A61K 47/48* (2006.01)
*C07F 9/09* (2006.01)
*C12P 17/10* (2006.01)

(52) U.S. Cl.
CPC ............ *A61K 47/481* (2013.01); *A61K 47/55* (2017.08); *A61K 47/62* (2017.08); *C07F 9/098* (2013.01); *C12P 17/10* (2013.01)

(58) Field of Classification Search
None
See application file for complete search history.

(56) References Cited

U.S. PATENT DOCUMENTS 4,938,949 A  7/1990  Borch et al.

OTHER PUBLICATIONS

Volkert 2003 "synthesis and biological activity of photoactivatable n-ras peptides and proteins" JACS 125:12749-12758 (Year: 2003).*

(Continued)

*Primary Examiner* — Adam Weidner
(74) *Attorney, Agent, or Firm* — Viksnins Harris Padys Malen LLP

(57) ABSTRACT

The present invention relates to triorthogonal reagents useful for site-specifically modifying a protein with two orthogonal groups that can be subsequently functionalized in a single one-pot procedure. This approach relies on the selective tagging of proteins containing an appended farnesyltransferase or geranylgeranyltransferase I substrate sequence. The incorporation of a bifunctional ethynyl-hydroxybenzaldehyde into the farnesyl or geranylgeranyl group facilitates the facile labeling of proteins with two different moieties.

25 Claims, 27 Drawing Sheets

(56) References Cited

OTHER PUBLICATIONS

Salgado, et al., "Metal-directed protein self-assembly", Acc Chem Res 43, 661-672 (2010).
Sletten, et al., "Bioorthogonal chemistry: fishing for selectivity in a sea of functionality", Angew Chem Int Ed Engl 48 (38), 6974-6998 (2009).
Sonogashira, et al., "Development of Pd—Cu catalyzed cross-coupling of terminal acetylenes with sp2-carbon halides", J Organometallic Chemistry, 653(1-2), 46-49 (2002).
Subramanian, et al., "Protein FarnesyltransferaseCatalyzed Isoprenoid Transfer to Peptide Depends on Lipid Size and Shape, not Hydrophobicity", CHEMBIOCHEM 9(17), 2872-2882 and Supporting Information, 76 pages (2008).
Uhlenheuer, et al., "Combining supramolecular chemistry with biology", Chem Soc Rev 39, 2817-2826 (2010).
Von Delius, et al., "A synthetic small molecule that can walk down a track", Nat Chem 2, 96-101 (2010).
Wang, et al., "Exploring post-translational arginine modification using chemically synthesized methylglyoxal hydroimidazolones", J Am Chem Soc 134, 8958-8967 (2012).
Weinrich, et al., "Oriented immobilization of farnesylated proteins by the thiol-ene reaction", Angew Chem Int Ed 49, 1252-1257 (2010).
Wen, et al., "CNTF and retina", Prog Retin Eye Res 31, 136-151 (2012).
Witte, et al., "Preparation of unnatural N-to-N and C-to-C protein fusions", Proc Natl Acad Sci 109, 11993-1198 (2012).
Yakhnin, et al., "Green fluorescent protein purification by organic extraction", Protein Expres Purif 14, 382-386 (1998).
Yi, et al., "One-pot dual-labeling of a protein by two chemoselective reactions", Angew Chem Int Ed Engl 50, 8287-8290 (2011).
Yin, et al., "Labeling proteins with small molecules by site-specific posttranslational modification", J Am Chem Soc 126, 7754-7755 (2004).
Zbinden, et al., "Selective and orally bioavailable phenylglycine tissue factor/factor VIIa inhibitors", Bioorg Med Chem Lett 15(23), 5344-5352 (2005).
Alexander, et al., "Mapping the Isoprenoid Binding Pocket of PDE[delta] by a Semisynthetic, Photoactivatable N-Ras Lipoprotein", ChemBioChem 10, 98-108 (2009).
Bertozzi, "A decade of bioorthogonal chemistry.", Acc. Chem. Res. 44, 651-653 (2011).
Brustad, et al., "A general and efficient method for the site-specific dual-labeling of proteins for single molecule fluorescence resonance energy transfer", J Am Chem Soc 130, 17664-17665 (2008).
Carlson, et al., "Chemically controlled self-assembly of protein nanorings", J Am Chem Soc 128 (23), 7630-7638 (2006).
Chen, et al., "Cyclodextrin-based inclusion complexation bridging supramolecular chemistry and macromolecular self-assembly", Chem Soc Rev 40, 2254 (2011).
Chen, et al., "Site-specific labeling of proteins with small molecules in live cells", Curr Opin Biotechnol 16, 35-40 (2005).
Christman, et al., "Site-specific protein immobilization through N-terminal oxime linkages", Journal of Materials chemistry 17, 2021-2027 (2007).
Discher, et al., "Polymer vesicles", Science 297, 967-973 (2002).
Distefano, et al., "Enzymatic Assembly of Fusion Proteins", Presentation at Protein Engineering Summit 2015, Boston, MA, May 5, 2015.
Distefano, "Enzymatic protein labeling using prenyltransferases for biomedical applications", Presenation at GTC Protein Discovery Summit 2016, Boston, MA, Dec. 7, 2016.
Dozier, et al., "An enzyme-coupled continuous fluorescence assay for farnesyl diphosphate synthases", Anal biochem 421, 158-163 (2012).
Duckworth, et al., "Site-specific, covalent attachment of proteins to a solid surface", Bioconjugate Chem 17, 967-974 (2006).
Fegan, et al., "Chemically controlled protein assembly: techniques and applications", Chem. Rev 110 (6), 3315-3336 (2010).
Fegan, et al., "Chemically self-assembled antibody nanostructures as potential drug carriers", Mol. Pharm. 9 (11), 3218-3227 (2012).
Feng, et al., "Bifunctional Unnatural Sialic Acids for Dual Metabolic Labeling of Cell-Surface Sialylated Glycans", J Am Chem Soc 135(25), 9244-9247 (2013).
Gangar, et al., "Programmable self-assembly of antibody-oligonucleotide conjugates as small molecule and protein carriers", J. Am. Chem. Soc., 134 (6), 2895-2897 (2012).
Gaon, et al., "Farnesyl and geranylgeranyl pyrophosphate analogs incorporating benzoylbenzyl ethers: Synthesis and inhibition of yeast protein famesyltransferase", Tetrahedron Letters 37(49), 8833-8836 (1996).
Gaon, et al., "Photoactive Analogs of Farnesyl Pyrophosphate Containing Benzoylbenzoate Esters: Synthesis and Application to Photoaffinity Labeling of Yeast Protein Farnesyltransferase", J Org Chem 61, 7738-7745 (1996).
Gauchet, et al., "Regio- and chemoselective covalent immobilization of proteins through unnatural amino acids", J Am Chem Soc 128, 9274-9275 (2006).
Guo, "The emerging field of RNA nanotechnology", Nat Nanotechnol 5(12), 833-842 (2010).
Hu, et al., "Assembly of nanoparticle-protein binding complexes: from monomers to ordered arrays", Angew Chem Int Ed Engl 46(27), 5111-5114 (2007).
Hudak, et al., "Synthesis of heterobifunctional protein fusions using copper-free click chemistry and the aldehyde tag", Angew Chem Int Ed 51, 4161-4165 (2012).
Ip, et al., "The neurotrophins and CNTF: two families of collaborative neurotrophic factors", Annu Rev Neurosci 19, 491-515 (1996).
Katadae, et al., "Interacting Targets of the Farnesyl of Transducin [gamma]-Subunit +", Biochemistry 47(32), 8424-8433 (2008).
Ke, et al., "Self-assembled water-soluble nucleic acid probe tiles for label-free RNA hybridization assays", Science 319, 180-183 (2008).
Keppler, et al., "Labeling of fusion proteins with synthetic fluorophores in live cells", Proc Natl Acad Sci 101, 9955-9959 (2004).
Kim, et al., "Simple and Efficient Strategy for Site-Specific Dual Labeling of Proteins for Single-Molecule Fluorescence Resonance Energy Transfer Analysis", Analytical Chemistry 85, 1468-1474 (2013).
Kim, et al., "Synthesis and activity of fluorescent isoprenoid pyrophosphate analogues", J Org Chem 69, 8186-8193 (2004).
Kim, et al., "Synthesis of bispecific antibodies using genetically encoded unnatural amino acids", J Am Chem Soc 134 (24), 9918-9921 (2012).
Labadie, et al. "Farnesyl diphosphate analogues with omega-bioorthogonal azide and alkyne functional groups for protein farnesyl transferase-catalyzed ligation reactions", J Org Chem 72, 9291-9297 (2007).
Lai, et al., "Localized protein interaction surfaces on the EntB carrier protein revealed by combinatorial mutagenesis and selection", J Am Chem Soc 128, 11002-11003 (2006).
Li, et al., "Chemically self-assembled antibody nanorings (CSANs): design and characterization of an anti-CD3 IgM biomimetic", J. Am. Chem. Soc. 132 (48), 17247-17257 (2010).
Li, et al., "Self-assembly of antibodies by chemical induction", Angew Chem Int Ed 47, 10179-10182 (2008).
Mamidyala, et al., "In situ click chemistry: probing the binding landscapes of biological molecules", Chem Soc Rev 39, 1252-1261 (2010).
Marecak, et al., "Benzoylphenoxy analogs of isoprenoid diphosphates as photoactivatable substrates for bacterial prenyltransferases", Bioorganic & Medicinal Chemistry Letters 7(15), 1973-1978 (1997).
Matsuura, et al., "Self-assembled synthetic viral capsids from a 24-mer viral peptide fragment", Angew Chem Int Ed Engl 49(50), 9662-9665 (2010).
Park, et al., "An interfacial oxime reaction to immobilize ligands and cells in patterns and gradients to photoactive surfaces", Langmuir 24, 6201-6207 (2008).

(56) References Cited

OTHER PUBLICATIONS

Patent Cooperation Treaty, International Searching Authority, Search Report and Written Opinion for PCT/US2014/060735, 12 pages, dated Jan. 29, 2015.

Pistol, et al., "Scalable, low-cost, hierarchical assembly of programmable DNA nanostructures", Nanotechnology 18, 125305 (2007).

Placzek, et al., "New synthetic methodology for the construction of 7-substituted farnesyl diphosphate analogs", Org Lett 13(14), 3576-3579 (2011).

Pompliano, et al., "Intramolecular fluorescence enhancement: a continuous assay of Ras farnesyl:protein transferase", J Am Chem Soc 114(20), 7945-7946 (1992).

Prescher, et al., "Chemistry in living systems", Nat Chem Biol 1, 13-21 (2005).

Prost, et al., "Noncarbohydrate glycomimetics and glycoprotein surrogates as DC-SIGN antagonists and agonists", ACS Chem Biol 7, 1603-1608 (2012).

Rashidian, et al., "A highly efficient catalyst for oxime ligation and hydrazone-oxime exchange suitable for bioconjugation", Bioconjugate Chem 24, 333-342 (2013).

Rashidian, et al., "Chemoenzymatic reversible immobilization and labeling of proteins without prior purification", J Am Chem Soc 134, 8455-8467 (2012).

Rashidian, et al., "Selective labeling of polypeptides using protein farnesyltransferase via rapid oxime ligation", Chem Commun 46(47), 8998-9000 (2010).

Rashidian, et al., "Simultaneous dual protein labeling using a triorthogonal reagent", J Am Chem Soc 135(44), 16388-16396 (2013).

Rashidian, "Site Specific Protein Labeling Using Farnesyl Transferase", Ph.D. Thesis, University of Minnesota, Sep. 2013.

Rhee, et al., "Function and mechanism of CNTF/LIF signaling in retinogenesis", Adv Exp Med Biol 664-647-654 (2010).

Rothemund, "Folding DNA to create nanoscale shapes and patterns", Nature 440, 297-302 (2006).

\* cited by examiner

A)

| Laser (nm) | Excite | Ex. Filter | Em. Filter | Color on the image |
|---|---|---|---|---|
| 405 | DAPI | DM405/488 | BA430/470 | Blue |
| 488 | GFP | DM405/488/543/635 | BA505/525 | Green |
| 543 | TAMRA | DM405/488/543/635 | BA560/660 | Red |

B)

| Laser (nm) | Excite | Ex. Filter | Em. Filter | Color on the image |
|---|---|---|---|---|
| 488 | GFP | DM405/488 | BA560/620 | Red |

Figure 25

SEQUENCE LISTING

```
<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1
```

```
Cys Val Ile Ala
1

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Cys Val Ile Ala
1               5
```

TRIORTHOGONAL REAGENTS FOR DUAL PROTEIN CONJUGATION

RELATED APPLICATIONS

This application claims priority to U.S. provisional application No. 61/891,262 filed on 15 Oct. 2013, the entire contents of which is incorporated herein by reference.

STATEMENT OF GOVERNMENT SUPPORT

This invention was made with government support under GM084152 awarded by NIH. The government has certain rights in the invention.

SEQUENCE LISTING

The instant application contains a Sequence Listing which has been submitted electronically in ASCII format and is hereby incorporated by reference in its entirety. Said ASCII copy, created on May 11, 2017, is named 09531_381US1_SL.TXT and is 726 bytes in size.

FIELD OF THE INVENTION

The present invention relates to reagents useful for simultaneously conjugating a protein to two bioorthogonal functional groups.

BACKGROUND OF THE INVENTION

Over the course of the last decade, bioorthogonal chemical methods have been developed for the site-specific chemical modification of proteins and used to alter their properties and function.[1-7] For example, fluorophores can be site-specifically attached to proteins as a biophysical or cellular localization tool, while protein-polymer conjugation is a well-established method for modulating the in vivo behavior of proteins.[8-11] In addition, a number of groups have reported bioorthogonal approaches for the construction of bifunctional protein assemblies. Schultz and co-workers coupled two antibody FABs via an alkyne-azide cycloaddition click reaction using non-natural mutagenesis techniques.[12] Bertozzi and coworkers, used an enzymatic formyl generating strategy[13] to generate an aldehyde that was then converted to a cyclooctyne- or azide-functionalized protein via oxime formation followed by reaction with other azide-modified peptides or proteins. Ploegh and coworkers used a variation of sortagging to create N-to-N and C-to-C protein conjugates by preparing pairs of azide- and alkyne-containing proteins that were then linked via click reactions.[14] In the above examples, proteins equipped with a single bioorthogonal group were modified with a second small molecule, polymer or protein bearing a complementary functional group.

Recently, progress towards the introduction of multiple functional groups into proteins has also been made. Wu and coworkers developed a strategy for site-specific two-color labeling of a Rab GTPase for FRET applications by applying chemoselective native chemical ligation and oxime ligation simultaneously.[15] A C-terminal oxime was generated via expression of a C-terminal thioester while an N-terminal cysteine (for subsequent ligation) was revealed by TEV-catalyzed proteolysis. In other work, Schultz and coworkers developed a method for site-specific dual-labeling of proteins for FRET analysis based on the use of selective cysteine alkylation combined with non-natural amino acid incorporation of a ketone moiety.[16] Park and coworkers successfully incorporated two unnatural amino acids bearing ketone and alkyne groups into a protein for analysis of protein dynamics using a related nonsense suppression approach.[17] Very recently, Chen and coworkers, designed and synthesized bifunctional sialic acid analogues containing azide and alkyne moieties for incorporation of two distinct chemical reporters into cellular sialylated glycans for FRET imaging.[18] While useful, that method is limited to sialylated-cell surface glycans and requires metabolic activation of the bifunctional sialic acid analogue to the corresponding CMP-sugar prior to incorporation.

Accordingly it would be desirable to provide new reagents for introducing multiple functional groups into proteins.

SUMMARY OF THE INVENTION

In one aspect of the invention there is provided a compound of formula I:

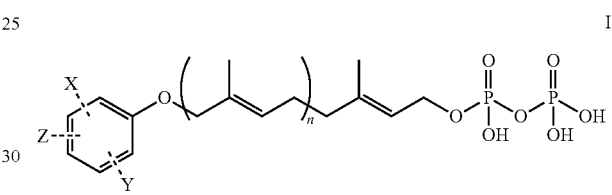

wherein X and Y are bioorthogonal groups that are identical or different which are capable of conjugating to a functional compound; Z is H, OH, halogen or haloalkyl; and n is an integer from 1 to 2.

In another aspect of the invention there is provided a method of functionalizing a protein having a CaaX motif, comprising:

(a) reacting said protein with a compound of formula I in the presence of a protein farnesyltransferase or a geranylgeranyltransferase I to produce a compound of formula II:

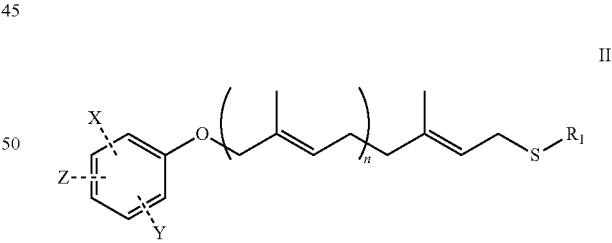

wherein

X, Y, Z and n are as defined herein; and $R_1$ is said protein which is attached to the remainder of the compound at the cysteine residue of the CaaX motif; and (b) reacting the compound of formula II with a first functional compound containing a reactive group that reacts with X to form a linkage to said first functional compound, and a second functional compound containing a reactive group that reacts with Y to form a linkage to said second functional compound, thereby forming a compound of formula III:

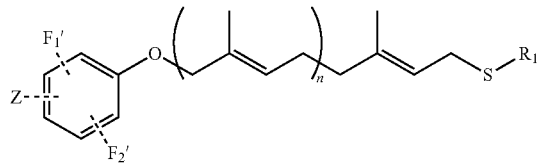

wherein $F_1'$ is a first functional group; and $F_2'$ is a second functional group.

BRIEF DESCRIPTION OF THE FIGURES

FIG. 1 discloses "CVIA" (N-term to C-term) as SEQ ID NO: 1 and "GCVIA" as SEQ ID NO: 2.

FIG. 5 discloses "CVIA" (N-term to C-term) as SEQ ID NO: 1.

FIG. 6 discloses "CVIA" (N-term to C-term) as SEQ ID NO: 1.

FIG. 7 discloses "CVIA" (N-term to C-term) as SEQ ID NO: 1.

FIG. 8 discloses "CVIA" (N-term to C-term) as SEQ ID NO: 1.

FIG. 9 discloses "CVIA" (N-term to C-term) as SEQ ID NO: 1.

FIG. 10 discloses "CVIA" (N-term to C-term) as SEQ ID NO: 1.

FIGS. 19A-D disclose "CVIA" (N-term to C-term) as SEQ ID NO: 1.

FIG. 20A discloses "CVIA" (N-term to C-term) as SEQ ID NO: 1.

FIG. 21A discloses "CVIA" (N-term to C-term) as SEQ ID NO: 1.

FIG. 22A discloses "CVIA" as SEQ ID NO: 1.

FIG. 25: A) Laser and filter settings for fluorescence experiments. B) Laser and filter settings for FRET between GFP and TAMRA.

DETAILED DESCRIPTION OF THE INVENTION

Figure 1:
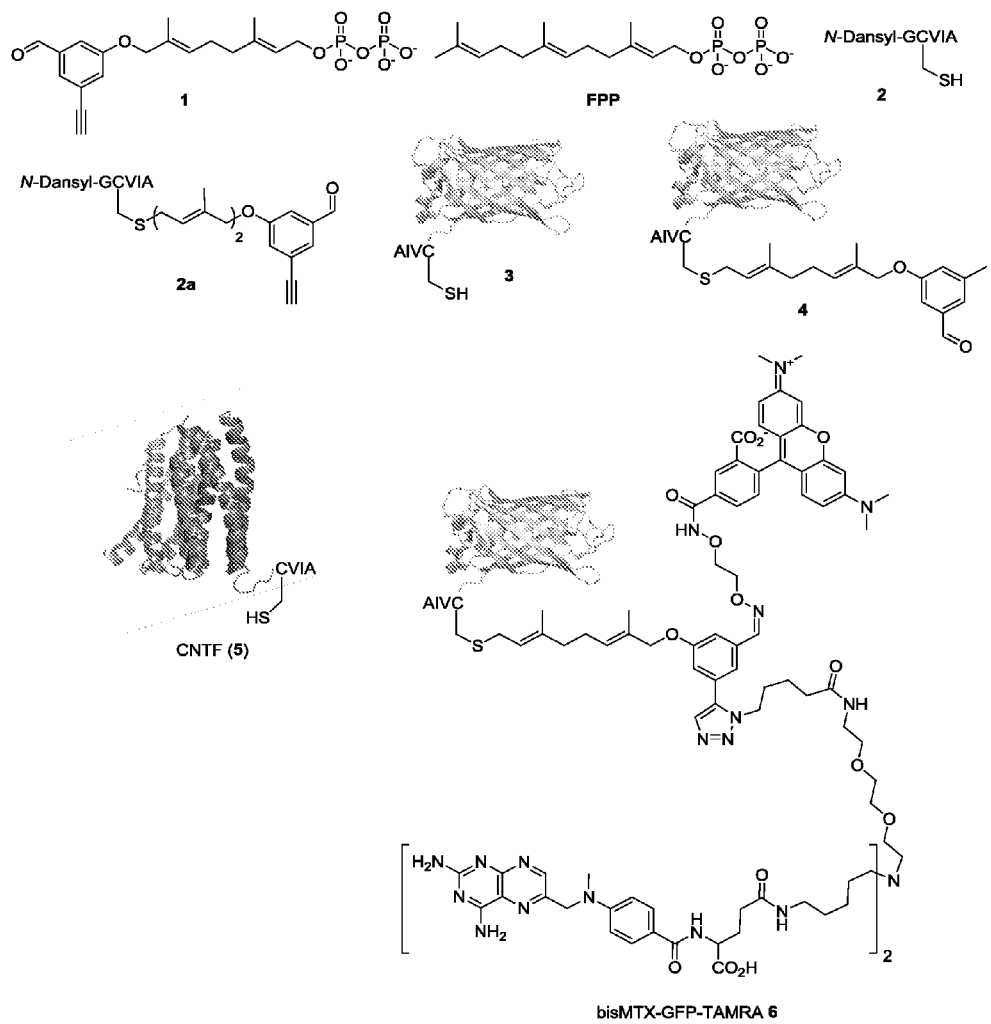
FIG. 1: Structures of compounds 1-6.
Figure 2:
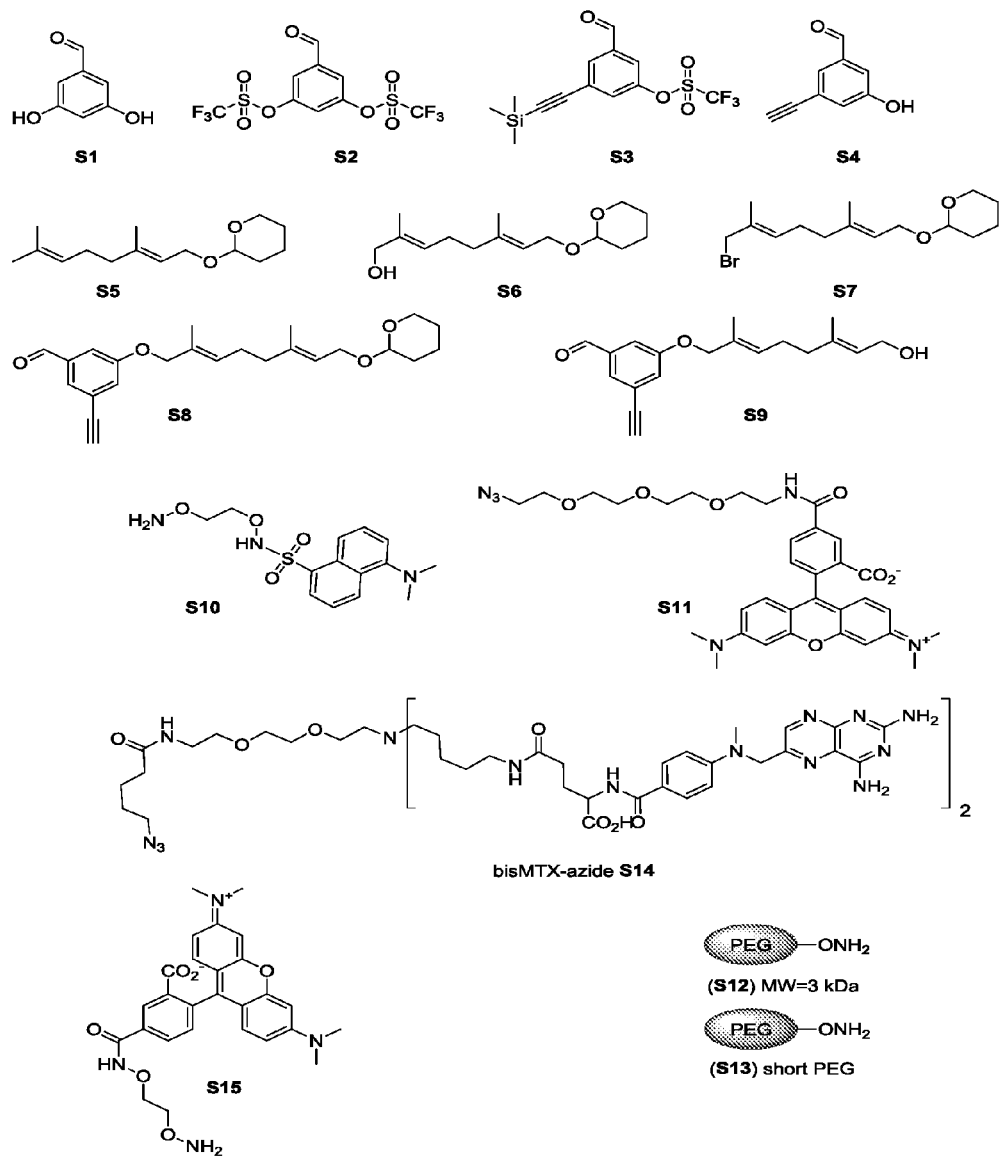
FIG. 2: Structures of compounds S1-S15.
Figure 3:
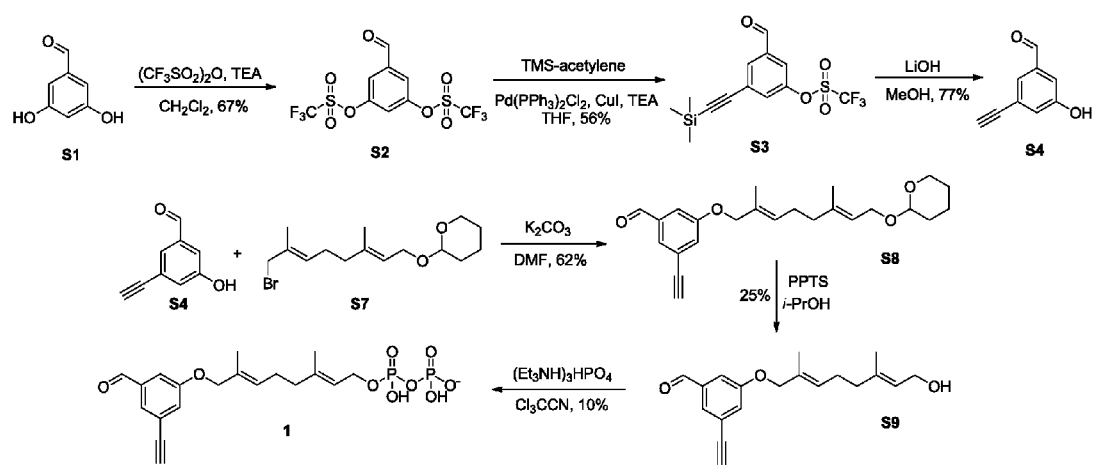
FIG. 3: Synthetic route for the preparation of compound 1.

The present invention relates to triorthogonal reagents useful for site-specifically modifying a protein with two orthogonal groups that can be subsequently functionalized in a single one-pot procedure. This approach relies on the selective tagging of proteins containing an appended farnesyltransferase or geranylgeranyltransferase I substrate sequence. The incorporation of a bifunctional ethynyl-hydroxybenzaldehyde into the farnesyl or geranylgeranyl group facilitates the facile labeling of proteins with two different moieties, thus expanding the potential capabilities of the tagged protein. For example, the alteration and monitoring of a potential therapeutic protein's biodistribution properties and pharmacokinetic behavior can be easily coupled. In addition, this approach can be used to direct the assembly of protein complexes, while monitoring their interactions with cells. Furthermore the present tri-functional bioconjugation approach may be used to enhance the plasma half-life of CAAX box PEGylated proteins by simultaneously monitoring their tissue distribution with an appended fluorophore or radiolabel. The methods herein may also be combined with other strategies[15-18] for bioorthogonal protein labeling to further tailor the properties of proteins or create more complex constructs thereof.

Accordingly, the present invention provides in one aspect a compound of formula I and a salt thereof:

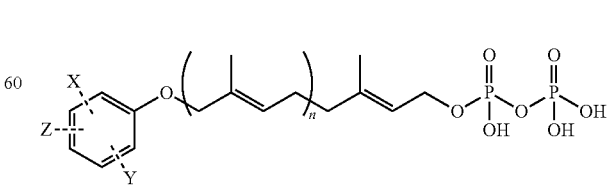

I wherein X and Y are bioorthogonal groups that are identical or different which are capable of conjugating to a functional compound; Z is H, OH, halogen or haloalkyl; and n is an integer from 1 to 2. In an embodiment, Z is H. In an embodiment, Z is halogen. In an embodiment, Z is F. In an embodiment, Z is $CF_3$. In an embodiment, n is 1. In an embodiment, n is 2.

Bioorthogonal groups are well known including those described by Sletten and Bertozzi[58]. In an embodiment, X and Y are independently selected from the group consisting of an alkyne, an alkene, an aminooxy group, a ketone, an aldehyde, an azide, a thioester, a hydrazine, a tetrazine, a trans-cyclooctene, a norbornene, an oxanorbornadiene, a triarylphosphine a diazirine and a benzophenone. In an embodiment, X and Y are linked to the phenoxy group of formula I via a stable linkage such as alkylene, aminoalkyl, alkylamino, alkoxy, or carboxamide. In another embodiment, X and Y are linked to the phenoxy group of formula I via a direct bond. In an embodiment, X and Y are the same. In another embodiment, X and Y are different.

In an embodiment, one of X and Y is an alkyne. In a particular embodiment, the alkyne is ethynyl. In another embodiment, the alkyne is a cyclooctyne.

In an embodiment X and Y are independently, —$(CH_2)_m$—C≡CH, —$(CH_2)_m$—CO—$(CH_2)_o$—H; —$(CH_2)_m$—$N_3$, —$(CH_2)_m$—NH—$NH_2$, or —$(CH_2)_m$—O—$NH_2$, wherein m is an integer from 0 to 6; and o is an integer from 0 to 3. In an embodiment one of X and Y is —C≡CH, —$N_3$, —NH—$NH_2$, or —O—$NH_2$.

In a particular embodiment, the compound is formula Ia or a salt thereof:

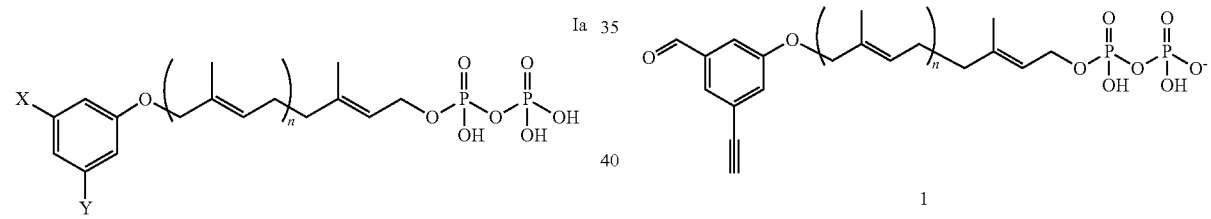

Ia wherein X, Y and n are as defined herein.

In another particular embodiment, the compound is formula Ib or a salt thereof:

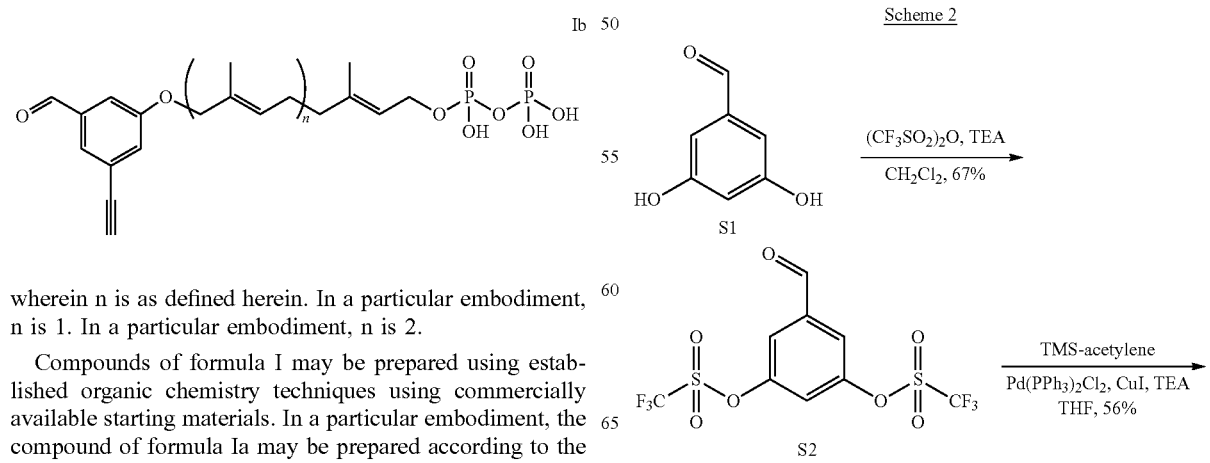

Ib wherein n is as defined herein. In a particular embodiment, n is 1. In a particular embodiment, n is 2.

Compounds of formula I may be prepared using established organic chemistry techniques using commercially available starting materials. In a particular embodiment, the compound of formula Ia may be prepared according to the following scheme 1 wherein n is as defined herein:

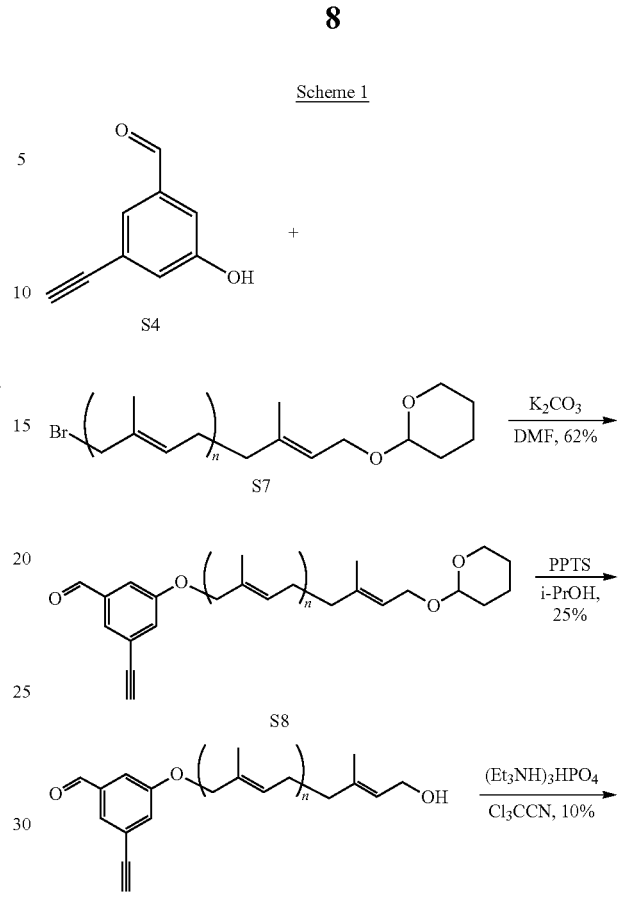

In another embodiment, compounds of formula I may be prepared according to the following scheme 2 wherein n is as defined herein:

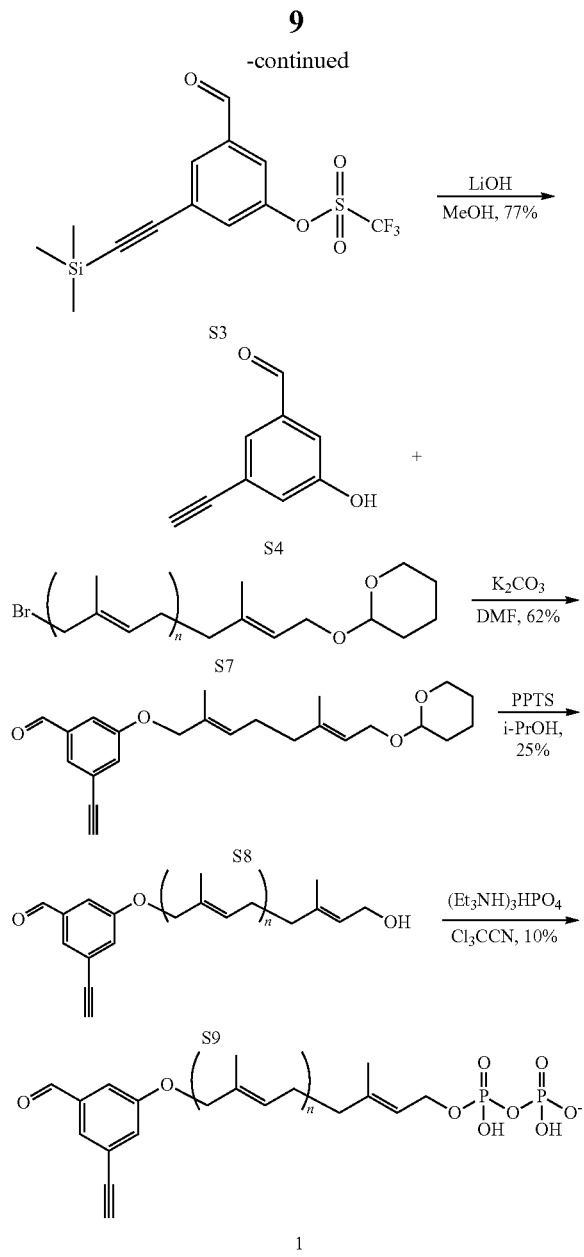

Compound 1 was synthesized from commercially available geraniol and 3,5-dihydroxybenzaldehyde in nine steps (Scheme 2). In brief, THP-protected geraniol was initially oxidized at C-8 to a terminal alcohol, followed by bromination of the hydroxyl group using $CBr_4$ and $PPh_3$. The 3,5-alkyne-aldehyde-functionalized phenol was prepared from 3,5-dihydroxybenzaldehyde via a Sonogashira Pd—Cu catalyzed cross-coupling reaction[29] in three steps. The modified phenol was alkylated with the aforementioned bromide using $K_2CO_3$ as the base. The THP group was removed and the alcohol was converted to the corresponding diphosphate via a direct phosphorylation strategy employing $(HNEt_3)_2HPO_4$ and $CCl_3CN$ as the activating reagent. Subsequent purification by RP-HPLC produced the desired bifunctional aldehyde-alkyne analogue 1 whose structure was confirmed by $^1$H-NMR, $^{31}$P-NMR, and HR-ESI-MS.

Figure 4:
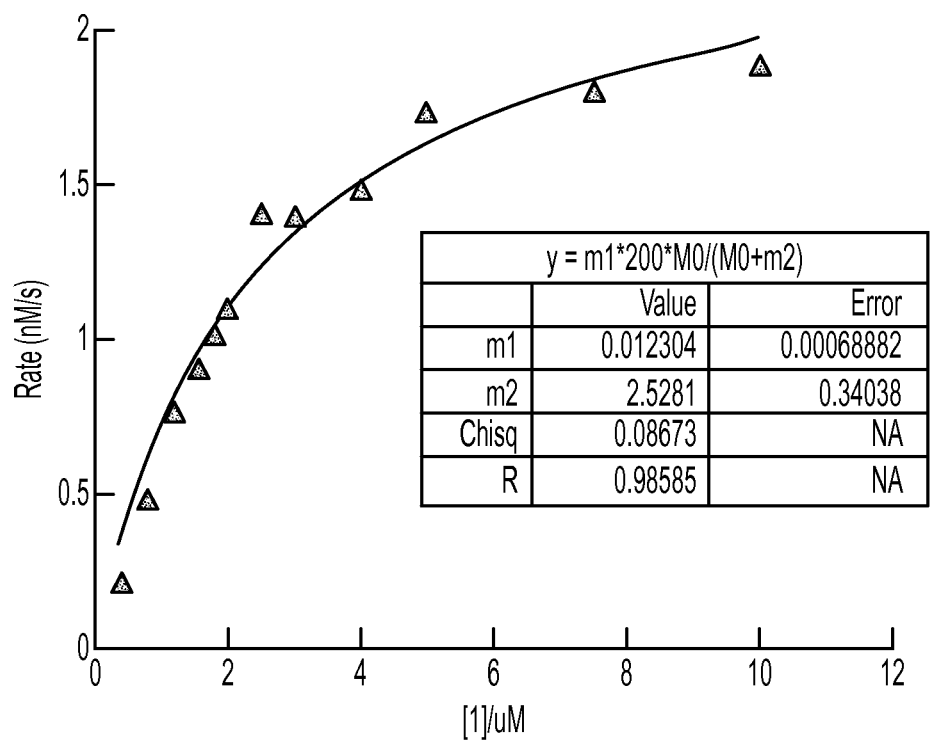
FIG. 4: Fluorescence-based PFTase enzyme assay for prenylation of model peptide 3 using varying concentrations of 1.
Figure 5:
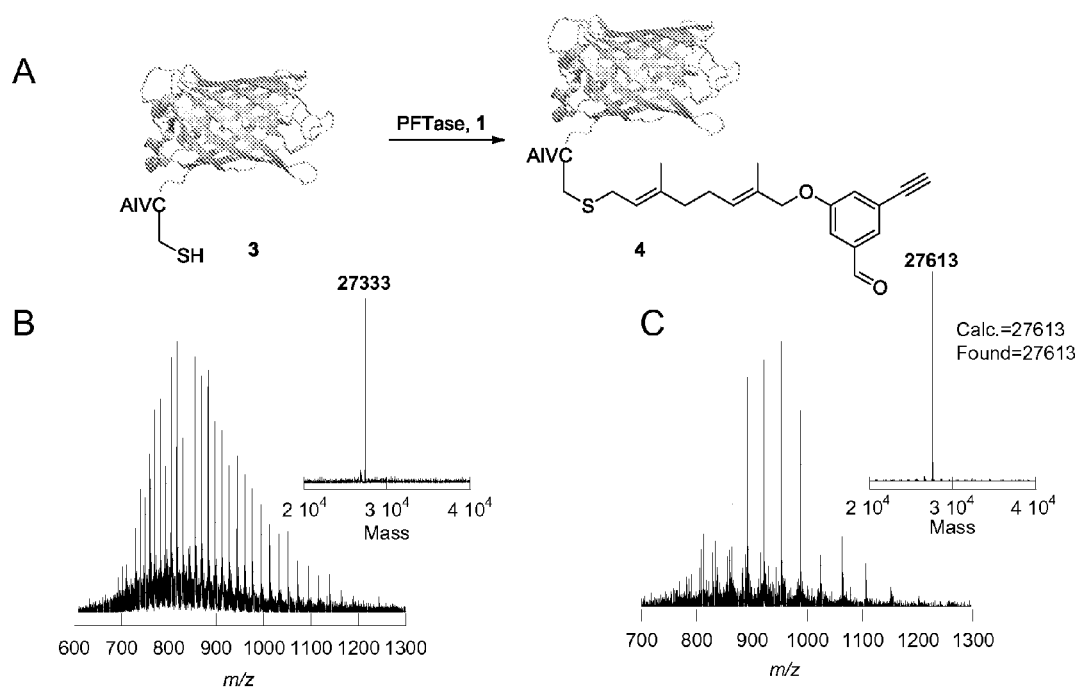
FIG. 5: Schematic representation of prenylation of GFP-CVIA (3) with FPP-analog 1 to yield functionalized GFP 4. ESI mass spectra of B) GFP-CVIA (3) and C) GFP prenylated with bifunctional analogue 1 to yield 4, showing successful prenylation of GFP 3. The deconvoluted mass spectra are shown in the insets.
Figure 6:
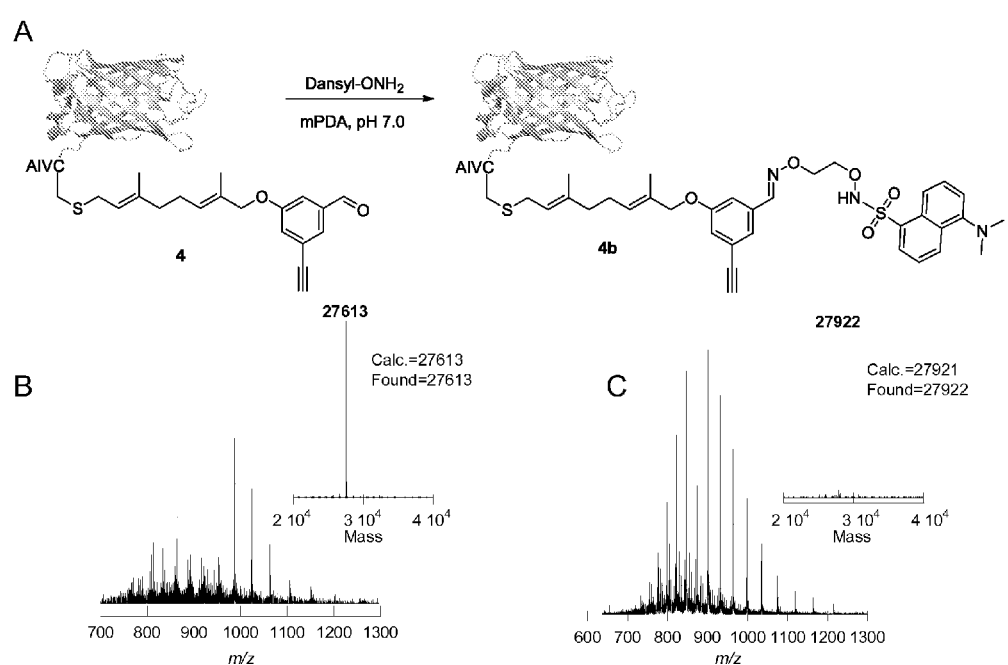
FIG. 6: A) Schematic representation of oxime ligation reaction between bifunctionalized-GFP (4) and aminooxy-dansyl (S10) to yield oxime-GFP (4b). ESI mass spectra of B) pure 4 and C) oxime-GFP 4b, indicating successful oxime ligation reaction. The deconvoluted mass spectra are shown in the insets.
Figure 7:
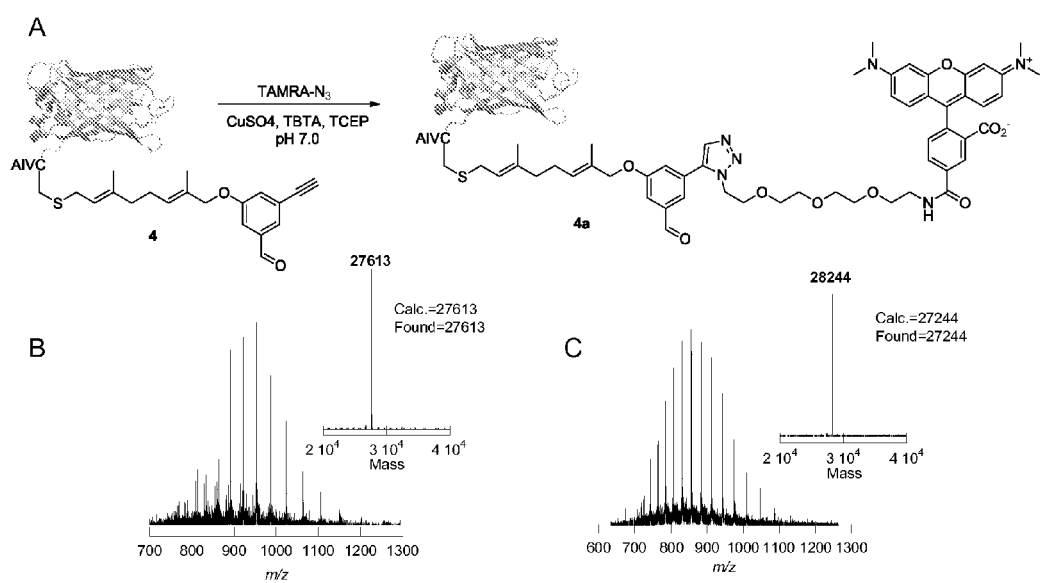
FIG. 7: A) Schematic representation of click reaction between the bifunctionalized-GFP 4 with azide-TAMRA S11 to yield labeled GFP 4a. ESI mass spectra of B) pure 4 and C) 4a, showing successful click reaction between S11 and 4. The deconvoluted mass spectra are shown in the insets.
Figure 8:
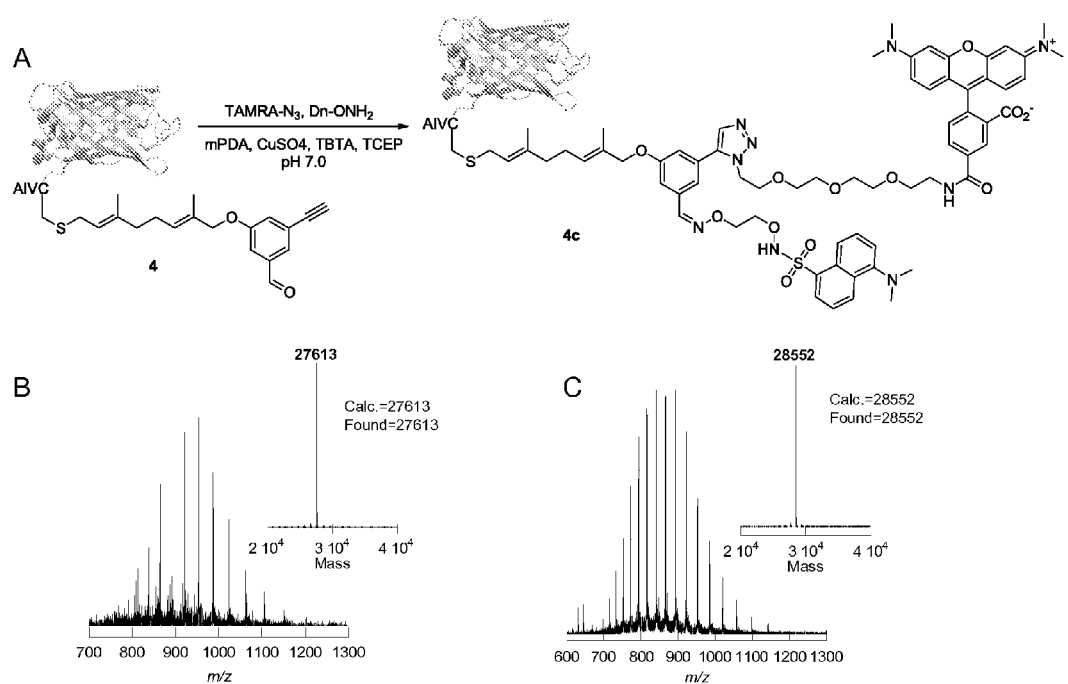
FIG. 8: A) Schematic representation of simultaneous click and oxime reactions between the bifunctionalized-GFP (4) with aminooxy-dansyl S10 and azido-TAMRA S11 to yield GFP 4c. ESI mass spectra of B) pure 4 and C) 4c, showing successful simultaneous click and oxime reactions between S10, S11 and 4. The deconvoluted mass spectra are shown in the insets.
Figure 9:
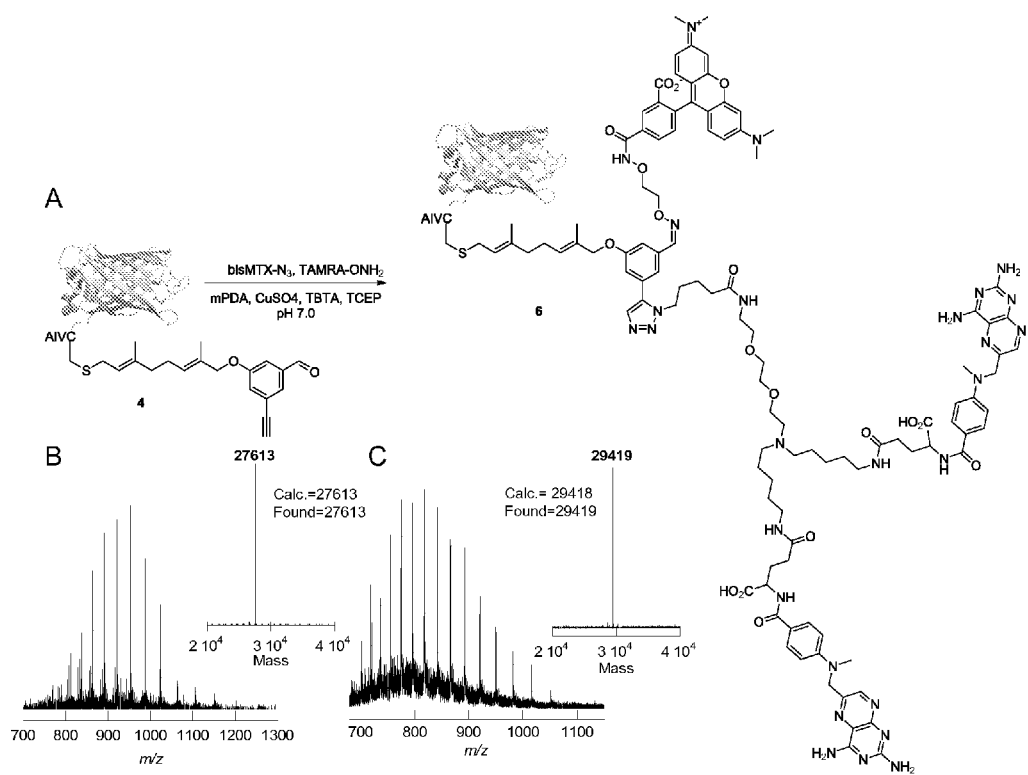
FIG. 9: A) Schematic representation of simultaneous click and oxime reactions between the bifunctionalized-GFP 4 with aminooxy-TAMRA S15 and azido-bisMTX S14 to yield GFP 6. ESI mass spectra of B) pure 4 and C) 6, showing successful simultaneous click and oxime reactions between 4, S14 and S15. The deconvoluted mass spectra are shown in the insets.
Figure 10:
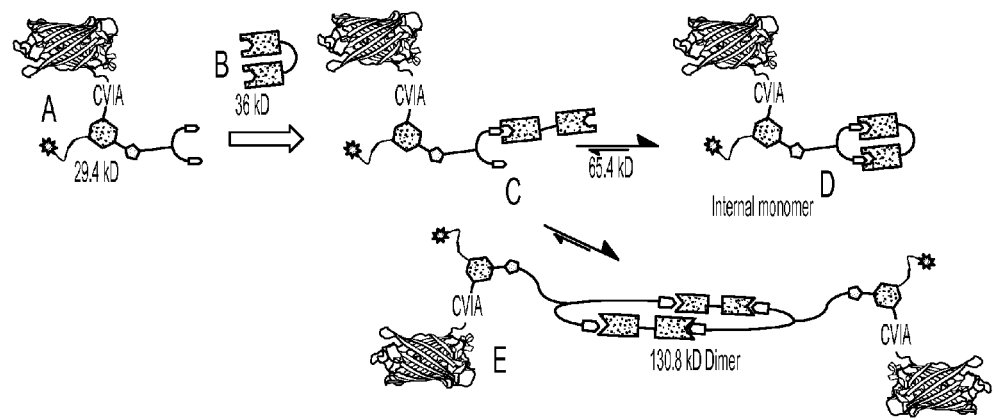
FIG. 10: Self-assembly of nanorings observed by SEC (13-DD with 6). Curve 4: bisMTX-GFP-TAMRA (6, Peak A). Curve 3: monomeric 13-DD (Peak B). Curves 1 and 2: induced oligomerization of 13-DD with 7 indicating the major products as the internal monomer (Peak D) and dimer (Peak C).
Figure 10:
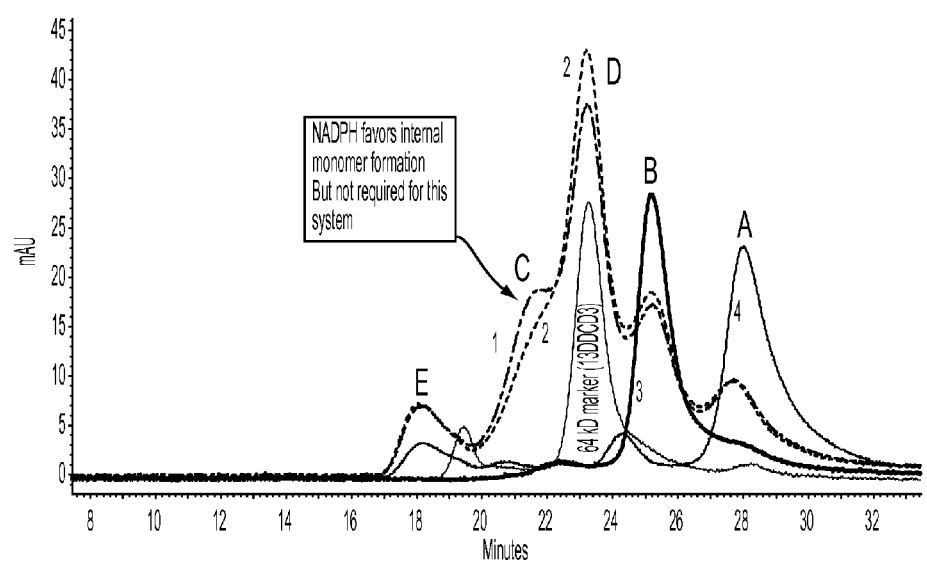
Figure 11:
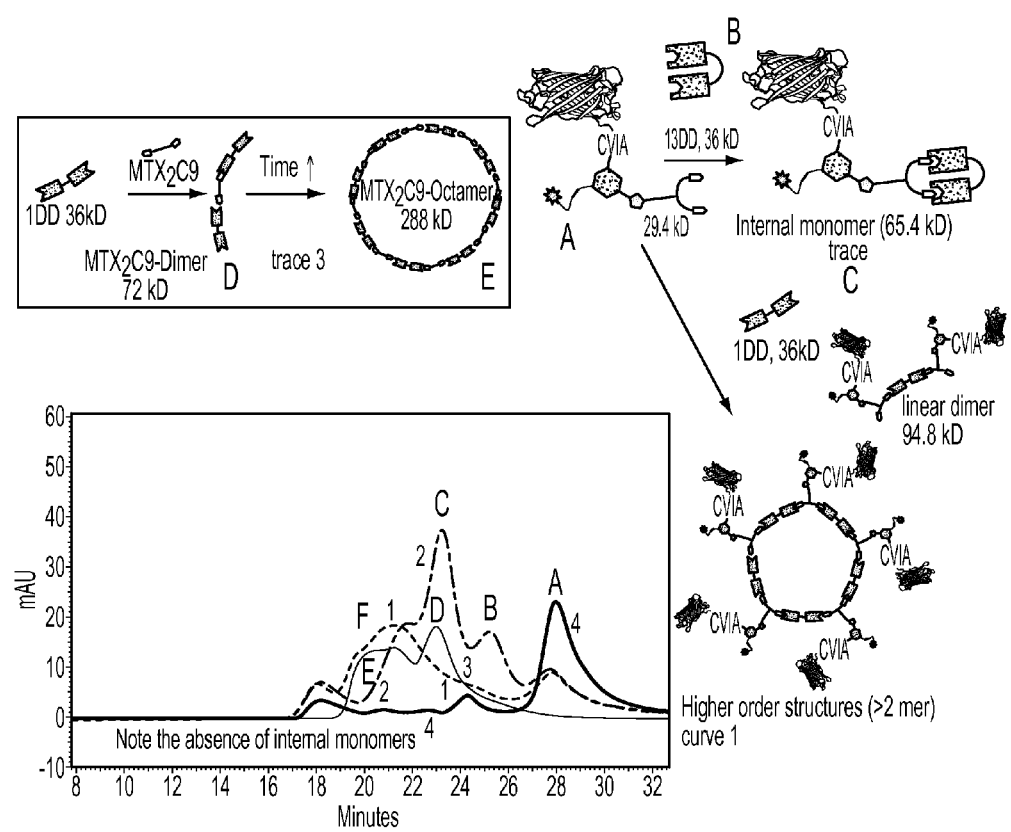
FIG. 11: Preliminary module studies of the self-assembly of nanorings observed by SEC (1-DD with 6). Curve 4: bisMTX-GFP-TAMRA (6, Peak A). Curve 2: induced oligomerization of 13-DD with 6 indicating the major products as the internal monomer (Peak C). Curve 1: induced oligomerization of 1-DD with 6 indicating the major products as the much higher order species. Curve 3: oligomerization of 1-DD with bisMTX-C9 dimerizer for comparison. Incomplete 1-DD-bisMTX octamerization due to short incubation time (1DD with $MTX_2C9$).

Initially, prenylation reactions containing a model peptide, N-dansyl-GCVIA (SEQ ID NO: 2) (2), analogue 1, and PFTase were performed and the reactions were monitored via a continuous fluorescence-based enzyme assay, as previously reported, 30 which demonstrated that compound 1 is an alternative substrate for the enzyme. Next, a kinetic analysis of that reaction was performed using varying concentrations of 1 and N-dansyl-GCVIA (SEQ ID NO: 2) (2) in the presence of PFTase showing that the enzymatic process obeyed saturation kinetics. Steady-state kinetic parameters for the prenylation reaction using the bifunctional aldehyde-alkyne analogue are shown in FIG. 4. This analysis revealed that the catalytic efficiency for alternative substrate 1 is reduced relative to that of FPP, with a kcat/KM value of 0.02 (relative to FPP). We found that a decrease in kcat constituted the major reason for the diminished catalytic activity with the analogue, with the kcat value for 1 (kcat=0.0123 s-1) observed to be 42-fold lower than the kcat for FPP (kcat=0.52 s-1), while no substantial difference was observed between the KM values for the analogue (KM=2.52 µM) and that of FPP (KM=1.71 µM) It should be noted that while the docking results suggest that 1 binds in a conformation similar to that of FPP, small differences are apparent in the vicinity of C-1 of the isoprenoid and the diphosphate which may account for the reduced reactivity. Nevertheless, despite this lower activity with 1, using elevated levels of PFTase (200 nM), it is relatively easy to drive these enzymatic reactions to completion in 2 hours.

Figure 19:
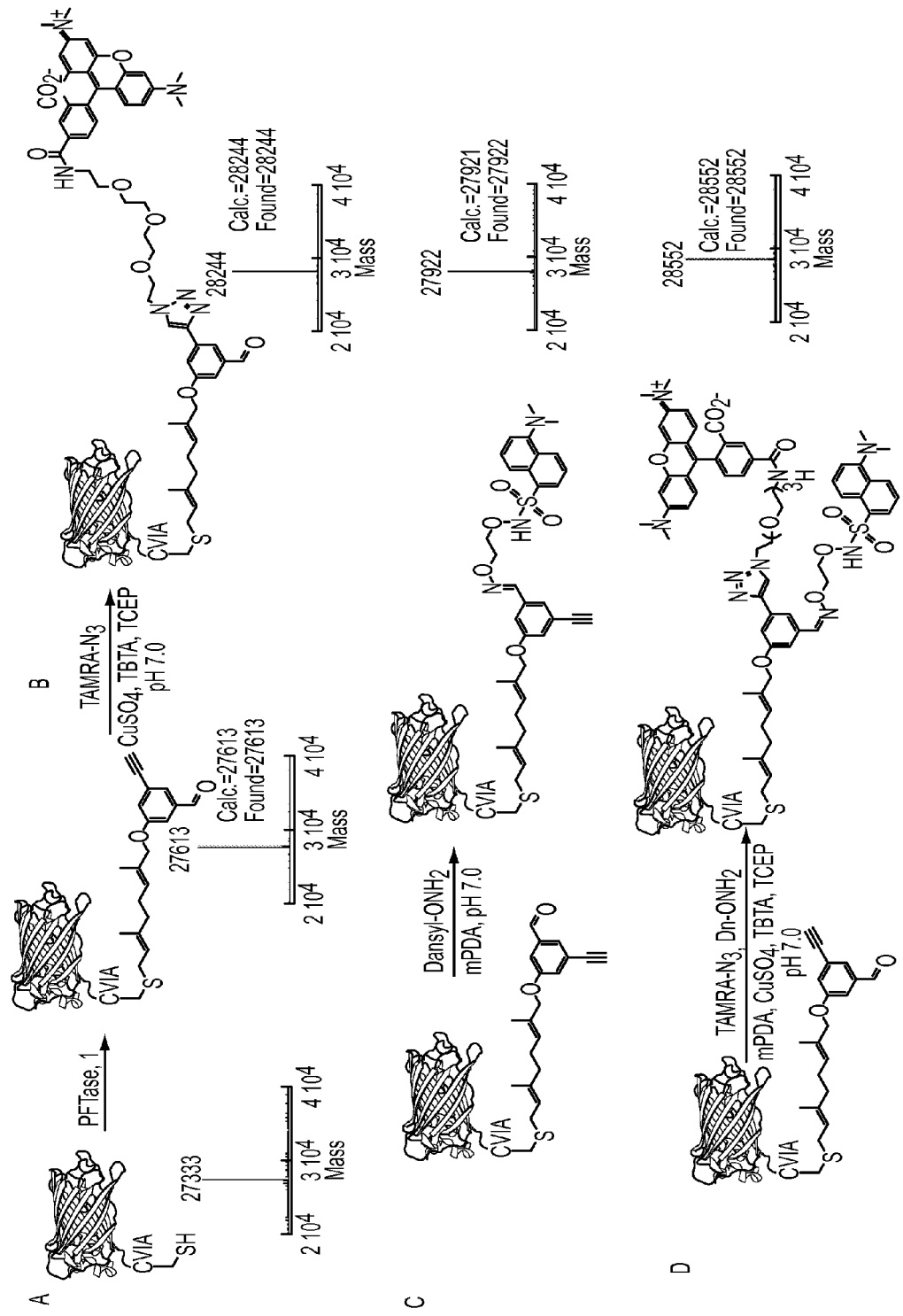
FIG. 19: A) Schematic representation of prenylation of GFP-CVIA (SEQ ID NO: 1) (3) with FPP-analogue 1 to yield bifunctionalized GFP 4. The deconvoluted mass spectra are shown adjacent to the compound structures showing successful prenylation of GFP 3. B) Schematic representation of click reaction between the bifunctionalized-GFP 4 with azido-TAMRA S11 to yield labeled GFP 4a. The deconvoluted mass spectrum of the clicked product is shown adjacent to the product, showing successful click reaction between S11 and 4. C) Schematic representation of oxime ligation reaction between bifunctionalized-GFP (4) and aminooxy-dansyl (S10) to yield oxime-GFP 4b. The deconvoluted mass spectrum is shown adjacent to the oxime product indicating successful oxime ligation reaction. D) Schematic representation of simultaneous click and oxime reactions between the bifunctionalized-GFP (4) with aminooxy-dansyl S10 and azido-TAMRA 511 to yield GFP 4c. The deconvoluted mass spectrum of the product is shown, showing successful simultaneous click and oxime reactions between S10, S11 and 4.

With the ability of analogue 1 to be incorporated by PFTase established, we next evaluated the utility of the analogue for selective protein modification. Accordingly, 1 was incubated with GFP-CVIA (SEQ ID NO: 1) (3) in the presence of PFTase (4 h, rt). That choice of reaction time was based on our earlier work with the peptide substrate N-dansyl-GCVIA (SEQ ID NO: 2) (2) where a 2 h reaction resulted in complete conversion. Concentration by ultracentrifugation followed by size-exclusion chromatography to remove excess 1 yielded pure bifunctionalized GFP 4 (FIG. 19A). Completion of the reaction was confirmed by LC-ESI/MS with the major peak corresponding to prenylated GFP (4) and a minor peak corresponding to a negligible amount of unreacted GFP-CVIA (SEQ ID NO: 1) (3).

In previous studies, we had shown that aldehyde-GFP and alkyne-GFP modified proteins could be derivatized to produce oxime-linked or clicked products, respectively.[23,27] In this study we explored simultaneous oxime and click reactions on a single prenylated-protein. First, to demonstrate the orthogonality of the two reactions, a separate oxime ligation or click reaction was carried out with the bifunctionalized protein. Thus, oxime ligation on 4 was performed with an aminooxy-dansyl reagent (S10) using m-phenylenediamine (mPDA) as the catalyst.[31] LC-MS analysis of the crude ligation reaction mixture confirmed complete conversion to the oxime-linked product 4b in less than 1 h (FIG. 19C). The click reaction was tested on 4 with azido-TAMRA (S11) using TCEP, TBTA and copper as the catalyst to yield GFP-TAMRA 4a (FIG. 19B). LC-MS analysis revealed that >80% conversion was obtained within 12 h of reaction, using equimolar concentrations of prenylated-protein and the coupling partner (azido-TAMRA, S11) as used in the above oxime ligation reaction (FIG. 19B). Typically the oxime ligation reaction proved to be modestly more efficient than the click reaction. When the oxime and click reactions were carried out simultaneously on the modified protein to yield 4c using equimolar concentrations of reagents (vide supra), quantitative conversion for the oxime reaction and ~90% conversion for the click reaction after 12 h was observed (FIG. 19D).

Figure 20:
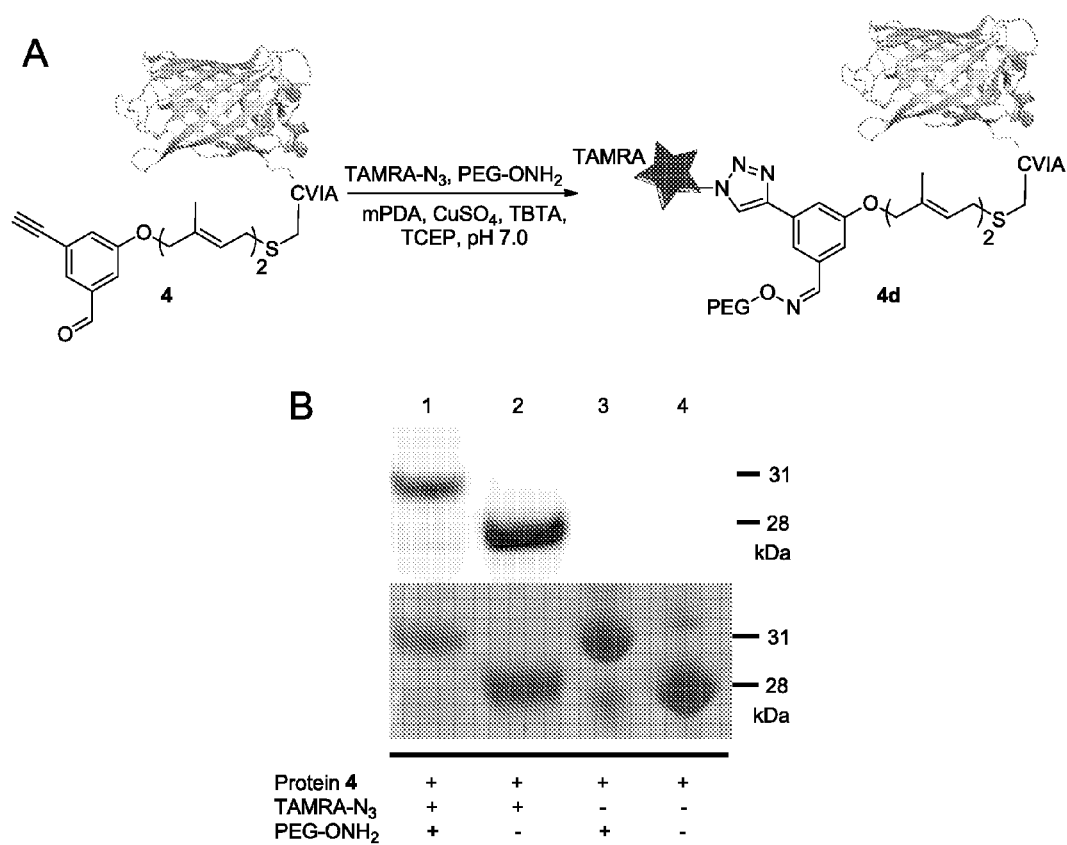
FIG. 20: A) Schematic representation of oxime ligation and click reaction of the bifunctionalized prenylated protein 4 with aminooxy-PEG (3 kDa) S12 and azido-TAMRA S11 followed by analysis of the reactions via SDS-PAGE. B) SDS-PAGE analysis of the aforementioned click and oxime reactions. Densitometry analysis on the SDS-PAGE of the reactions in part C revealed highly selective and almost complete (>95%) conversions for both oxime and click reactions on the prenylated protein. The lower bands were visualized by staining with Coomassie blue while the upper bands were detected via in-gel fluorescence imaging of TAMRA. Lane 1: reaction mixture contains protein 4, PEG-ONH2 and TAMRA-N3; lane 2: reaction mixture contains protein 4and TAMRA-N3; lane 3: reaction mixture contains protein 4 and PEG-ONH2; lane 4: solution contains only protein 4. Densitometry analyses were performed using the program ImageJ v1.46.

After optimizing the conditions for the oxime and click reactions on the bifunctional prenylated protein 4, we next evaluated the preparation of a PEG-GFP-TAMRA, 4d (FIG. 20). We chose TAMRA and PEG as examples because the fluorophore can act as a biophysical or cellular localization tool while the PEG can improve protein pharmacokinetics. Protein 4 was incubated first with azido-TAMRA (S11)

under the optimized click reaction conditions described above for 12 h. LC-MS analysis on the reaction mixture revealed complete conversion of bifunctionalized protein 4 to GFP-TAMRA (4a). Subsequently, the product was incubated with aminooxy-PEG (3 kDa) (S12, from Quanta BioDesign) at pH 7 in presence of mPDA (40 mM) as a catalyst for 2 h. SDS-PAGE analysis of the aforementioned reactions revealed highly selective and almost complete (>95%) conversions for both oxime and click reactions with the prenylated protein (FIG. 20). The lower bands (FIG. 20) were visualized by staining with Coomassie blue while the upper bands were detected via in-gel fluorescence imaging of TAMRA. That data showed that the reaction mixture including protein 4, aminooxy-PEG and azido-TAMRA contained a species with lower mobility in the SDS-PAGE gel due to the higher mass obtained upon addition of the PEG group; a dark band was also observed via in-gel fluorescence imaging of TAMRA (FIG. 20, Lane 1) that comigrated with the lower mobility species noted above. When no PEG reagent was present in the reaction mixture, the lower mobility band was absent (Lane 3) and when azido-TAMRA was not present in the reaction, only the higher mobility species that migrated near the starting protein was fluorescently labeled. Taken together, these results establish that two different functionalities can be installed simultaneously into a protein via two distinct bioorthogonal reactions using this triorthogonal labeling strategy.

Figure 21:
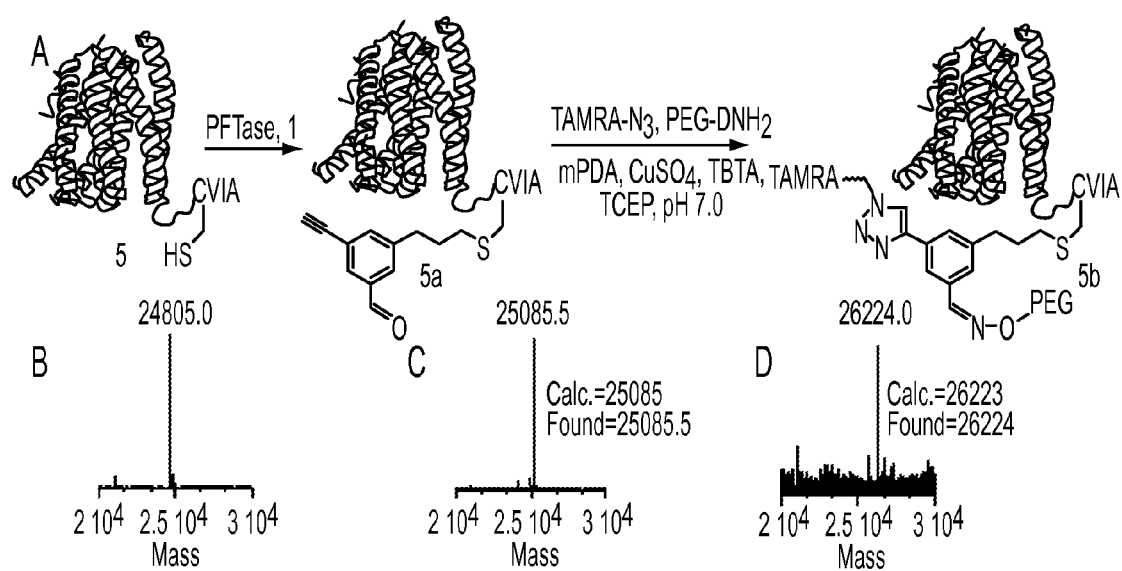
FIG. 21: Prenylation of CNTF-CVIA (SEQ ID NO: 1) (5) with FPP analogue 1 followed by simultaneous fluorophore labeling and PEGylation of the prenylated protein 5a via click and oxime ligations with azido-TAMRA S11 and aminooxy-PEG S13 to yield 5b. B,C and D) The deconvoluted mass spectra are shown, showing successful prenylation (B is pure CNTF and C is the prenylated-CNTF) and simultaneous click and oxime reactions (D).
Figure 22:
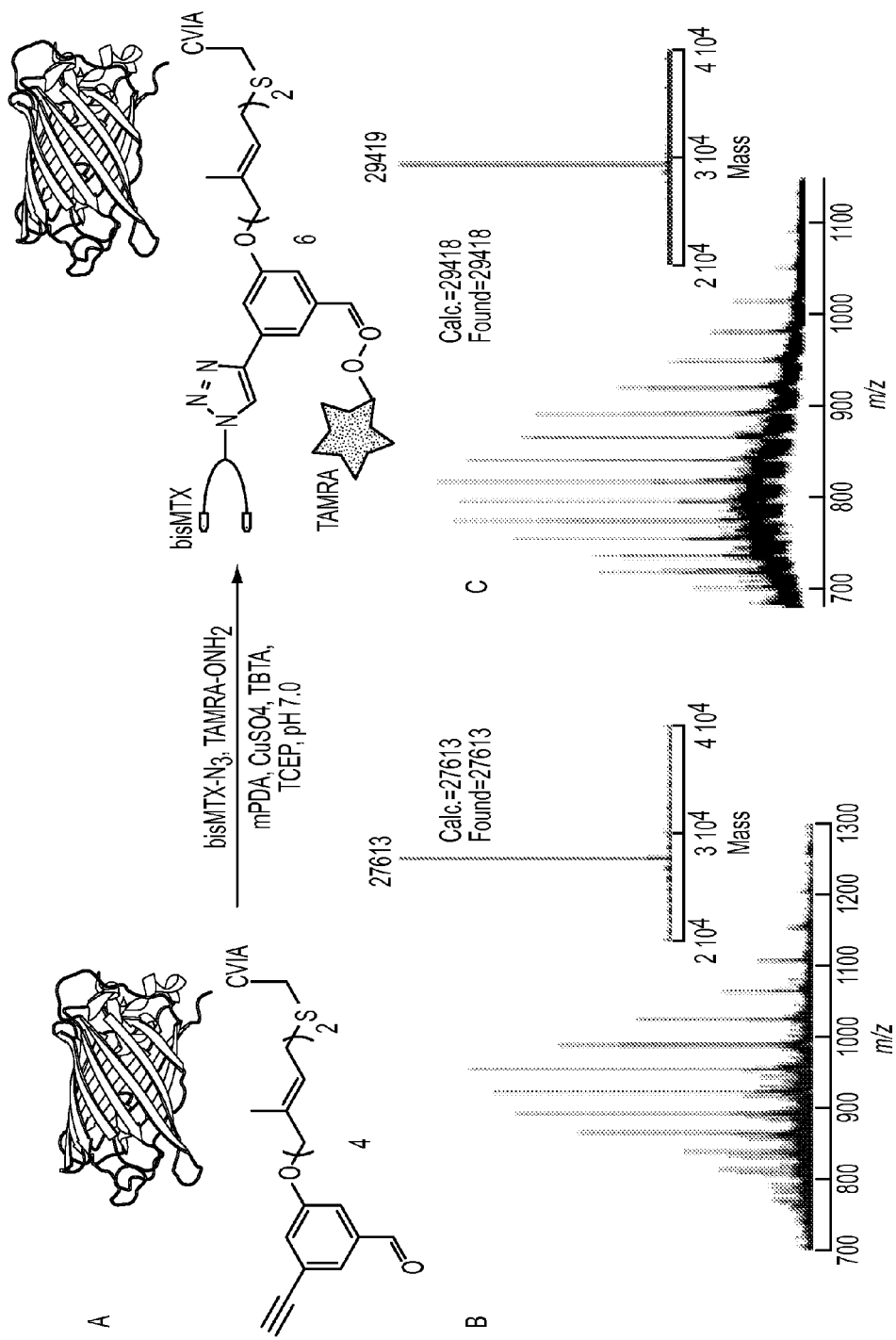
FIG. 22: A) Schematic representation of simultaneous oxime ligation and click reaction of the bifunctionalized prenylated protein 4 with azido-bis-MTX S14 and aminooxy-TAMRA S15. B and C) ESI MS analysis of 4 and 6 with the deconvoluted mass spectra shown in the insets, respectively.
Figure 23:
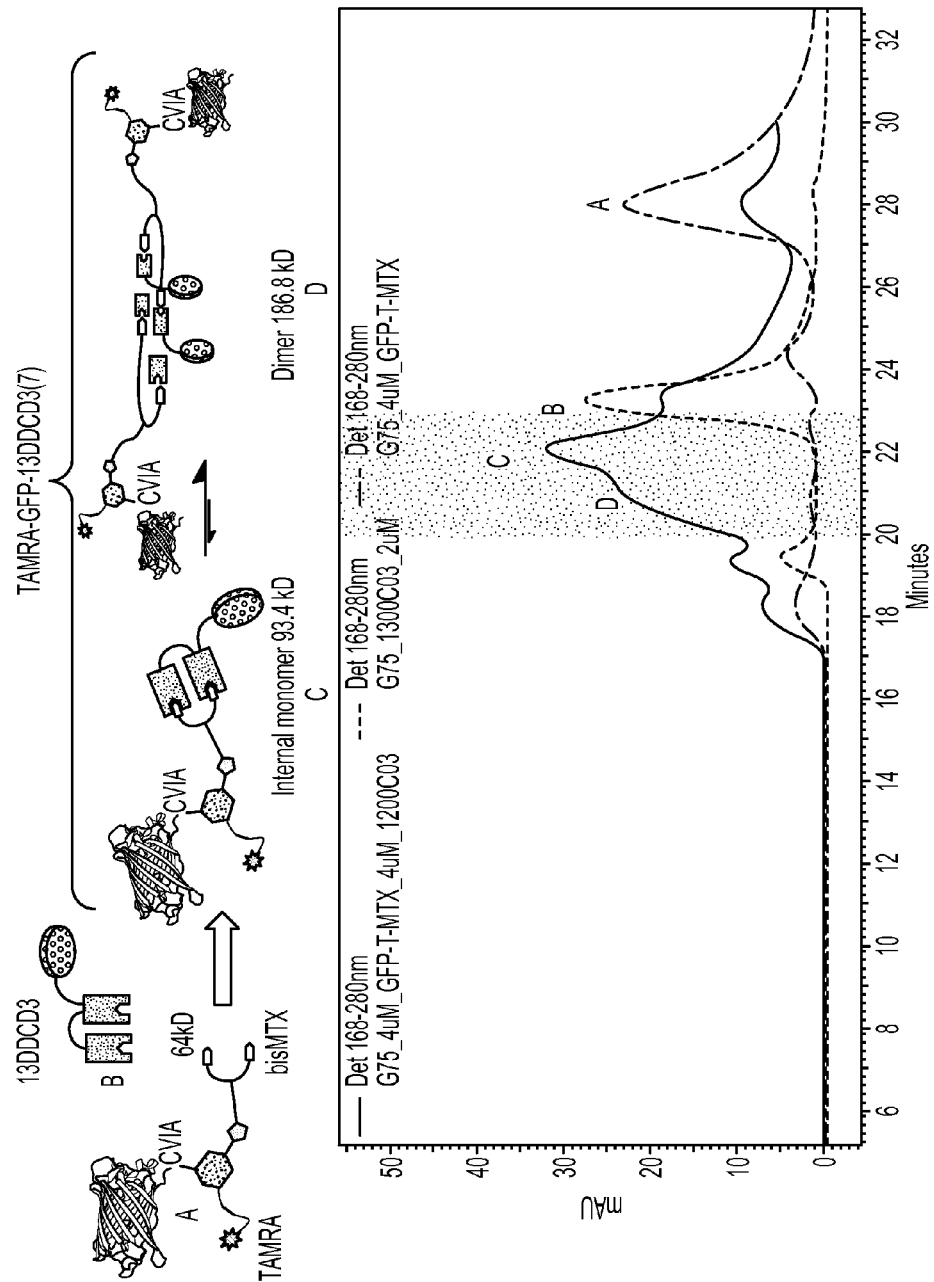
FIG. 23: Self-assembly of antibody nanorings 7 observed by SEC (13DDCD3 with 6). Blue curve: bis-MTX-GFP-TAMRA (6, Peak A). Green curve: monomeric 13DDCD3 (Peak B). Black curve: induced oligomerization of 13DDCD3 with 6 indicating the major products as the internal monomer (Peak C) and dimer (Peak D); Shaded area indicates the material collected and used for subsequent biological studies. HP-SEC was performed using a Superdex G75 column with a flow rate of 0.5 mL/min and monitoring at 280 nm.

Having established the utility of this method for C-terminal site-specific modification with a model protein, GFP, we decided to illustrate its use by modifying a biomedically important protein. Ciliary Neurotrophic Factor (CNTF) is a member of a class of proteins that promote neuron survival during inflammatory events and can stimulate neurite outgrowth.[32] Recently, CNTF has been studied extensively as a possible therapeutic agent for slowing retinal degeneration.[33,34] Thus, we elected to investigate the preparation of a bifunctionalized CNTF using the new strategy reported here. To accomplish this, purified CNTF-CVIA (SEQ ID NO: 1) (5),[31] a form of CNTF engineered to contain a C-terminal CAAX box, was prenylated with analogue 1 followed by labeling using azido-TAMRA S11 and PEGylation with aminooxy-PEG S13. LC-MS analysis (FIG. 21) confirmed successful prenylation and subsequent modification of CNTF by both azido-TAMRA and aminooxy-PEG S13.

In another aspect of the invention there is provided a method of functionalizing a protein having a CaaX motif, comprising:

(a) reacting said protein with a compound of formula I in the presence of a protein farnesyltransferase or a geranylgeranyltransferase I to produce a compound of formula II:

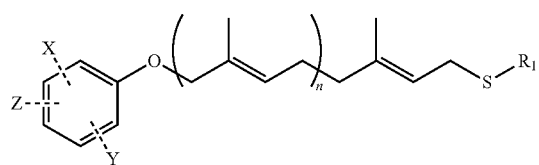

II wherein

X, Y, Z and n are as defined herein; and $R_1$ is said protein which is attached to the remainder of the compound at the cysteine residue of the CaaX motif; and (b) reacting the compound of formula II with a first functional compound containing a reactive group that reacts with X to form a linkage to said first functional compound, and a second functional compound containing a reactive group that reacts with Y to form a linkage to said second functional compound, thereby forming a compound of formula III:

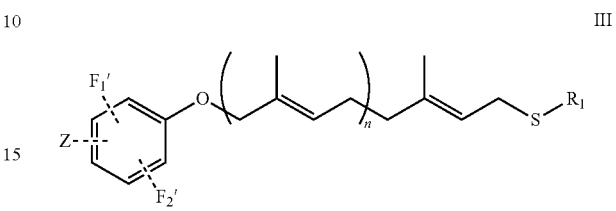

III wherein $F_1'$ is a first functional group; and $F_2'$ is a second functional group. In a particular embodiment F1 and F2 are independently $F_1$ and $F_2$ are functional compounds containing reactive groups that react with X and Y of compounds of formula II respectively to provide the functionalized protein compound of formula III in which the compounds upon conjugation to compound of formula II, provide functional groups $F_1'$ and $F_2'$ respectively in compound of formula III. $F_1$ and $F_2$ may be the same or different and may be proteins, small molecules or polymers. In a particular embodiment $F_1$ and $F_2$ are different functional compounds providing different functional groups $F_1'$ and $F_2'$. In an embodiment, at least one of $F_1$ and $F_2$ are a polymer. In a particular embodiment the polymer is $F_1$ contains an azide group that reacts with the ethynyl group of the compound of formula II to form a triazole linkage to the functional group $F_1'$ in the compound of formula III. In a particular embodiment, $F_1$ is azido-TAMRA fluorophore. In another embodiment, $F_1$ is an azide-functionalized spin label. In another embodiment, $F_1$ is a azide-functionalized radioactive molecule useful for imaging. In another embodiment, $F_1$ is azido-bis-methotrexate. In another embodiment, $F_1$ is a toxic molecule such as azide-functionalized vedotin. In another embodiment, $F_1$ is a drug such as azide-functionalized doxorubicin. In another embodiment, $F_1$ is a protein containing an azide group. In another embodiment, $F_1$ is a segment of nucleic acid containing an azide group. In a particular embodiment, $F_2$ contains a aminooxy group that reacts with the formyl group of the compound of formula II to provide an oxime linkage to the functional group $F_2'$ in the compound of formula III. In a particular embodiment, $F_2$ is aminooxy-PEG. In another embodiment, $F_2$ is aminooxy-TAMRA. In another particular embodiment, $F_2$ contains a hydrazine group that reacts with the formyl group of the compound of formula II to provide an hydrazone linkage to the functional group $F_2'$ in the compound of formula III.

Table 1 describes possible bioorthogonal groups within X and Y which react with a binding partner contained in a functional compound and the resulting linkage type.

TABLE 1

| X/Y | binding partner | linkage |
|---|---|---|
| tetrazine | trans-cyclooctene | cycloocta[d]pyridazine |
| tetrazine | norbornene | methanophthalazine |
| trans-cyclooctene | tetrazine | cycloocta[d]pyridazine |

TABLE 1-continued

| X/Y | binding partner | linkage |
| --- | --- | --- |
| norbornene | tetrazine | cycloocta[d]pyridazine |
| tetrazole | alkene | dihydropyrazole |
| alkene | tetrazole | dihydropyrazole |
| azide | alkyne | triazole |
| azide | oxanorbornadiene | triazole |
| azide | triarylphosphine | amide, alkoxyimindate |
| alkyne | azide | triazole |
| oxanorbornadiene | azide | triazole |
| triarylphosphine | azide | amide, alkoxyimindate |
| diazirine | amino acid residues | —C—C— |
| diazirine | alkene | cyclopropyl |
| alkene | diazirine | cyclopropyl |
| aldehyde/ketone | aminooxy | oxime |
| aminooxy | aldehyde/ketone | oxime |
| aldehyde/ketone | hydrazine | hydrazone |
| hydrazine | aldehyde/ketone | hydrazone |
| thioester | cysteine | amide |
| benzophenone | amino acid residues | —C—C— |

In an embodiment, X or Y is a s-tetrazine or trans-cyclooctene. A ligation reaction of a trans-cyclooctene and an s-tetrazine in an inverse-demand Diels Alder reaction followed by a retro-Diels Alder reaction to eliminate nitrogen gas. The reaction is extremely rapid with a second order rate constant of 2000 $M^{-1}$ $s^{-1}$ (in 9:1 methanol/water) allowing modifications of biomolecules at extremely low concentrations.

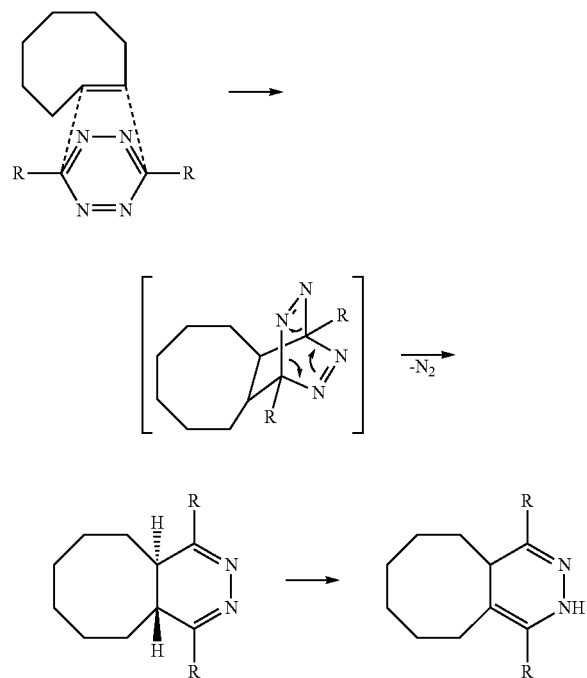

In a particular embodiment, there is provided a method of functionalizing a protein having a CaaX motif, comprising:

(a) reacting said protein with a compound of formula I in the presence of a protein farnesyltransferase or a geranylgeranyltransferase I to produce a compound of formula II:

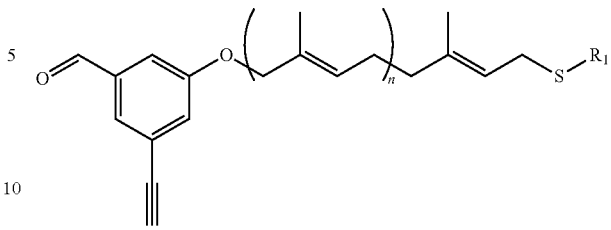

wherein n is an integer from 1 to 2; and $R_1$ is said protein which is attached to the remainder of the compound at the cysteine residue of the CaaX motif; and (b) reacting the compound of formula II with a first functional compound containing an azide group that reacts with the ethynyl group of the compound of formula II to form a triazole linkage thereto, and a second functional compound containing a reactive aminooxy or hydrazine group that reacts with the formyl group of the compound of formula II to form an oxime or hydrazone linkage thereto, thereby forming a compound of formula III:

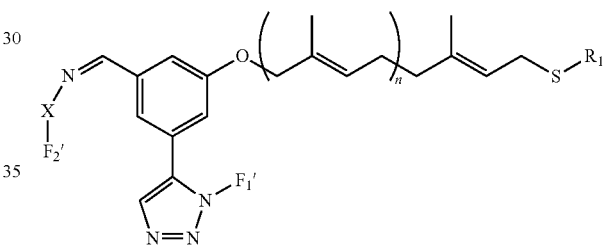

wherein

X is O or NH;

$F_1'$ is a first functional group; and $F_2'$ is a second functional group.

In an embodiment, n is 1 and the protein $R_1$ is reacted with a compound of formula I in the presence of the enzyme farnesyltransferase. In another embodiment, n is 2 and the protein is reacted with a compound of formula I in the presence of the enzyme geranylgeranyltransferase I. $R_1$ is a protein comprising CaaX motif wherein the protein is attached to the remainder of the compound of formula II via a thiol linkage at the cysteine residue of the CaaX motif, i.e. the sulfur atom shown in formula II is from CaaX moiety cysteine side chain. In an embodiment of the invention, the protein $R_1$ is an antibody.

Figure 12:
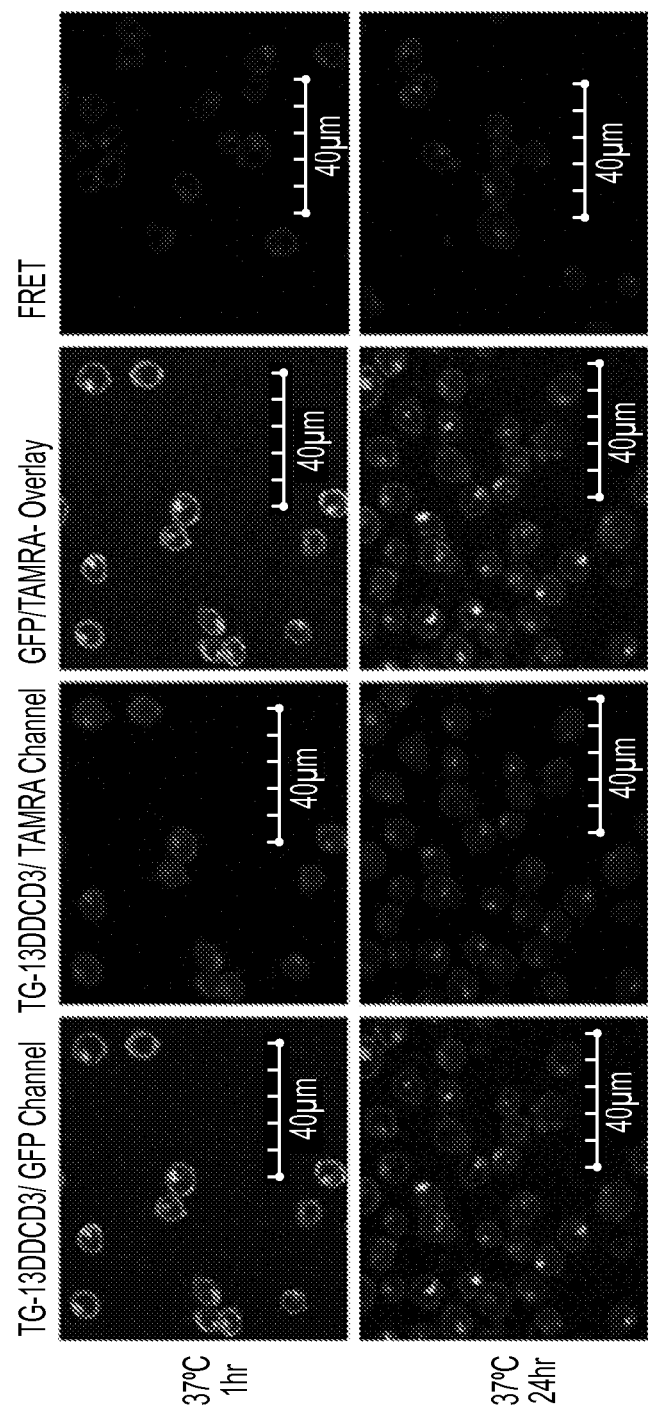
FIG. 12: Imaging of HPB-MLT cells treated with 7 (TG-13DDCD3) at 37° C. for 1 h (top panel) and for 24 h (bottom panel). A & E: GFP channel; B & F: TAMRA channel; C &G: Overlay of the GFP and TAMRA channels indicate the intact assembled protein (co-localized yellow punctuates); D & H: Observed FRET between GFP and TAMRA using above-mentioned filter settings. (FRET images were acquired right after GFP and TAMRA imaging and shows a different area of the same slide) Magnification: 40×.
Figure 13:
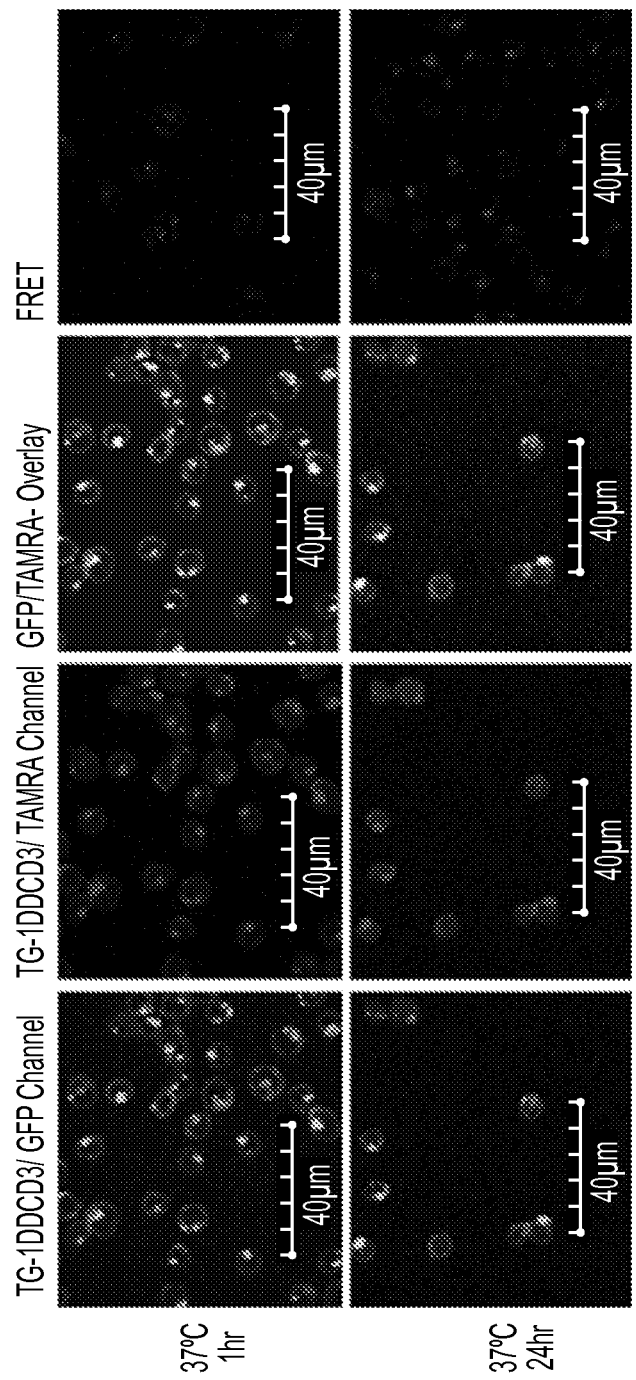
FIG. 13: Imaging of HPB-MLT cells treated with 8 (TG-1DDCD3) at 37° C. for 1 h (top panel) and for 24 h (bottom panel). A & E: GFP channel; B & F: TAMRA channel; C &G: Overlay of the GFP and TAMRA channel indicates intact assembled protein (co-localized yellow punctuates); D & H: Observed FRET between GFP and TAMRA using above-mentioned filter settings. (FRET images were acquired right after GFP and TAMRA imaging and shows a different area of the same slide) Magnification: 40×.
Figure 14:
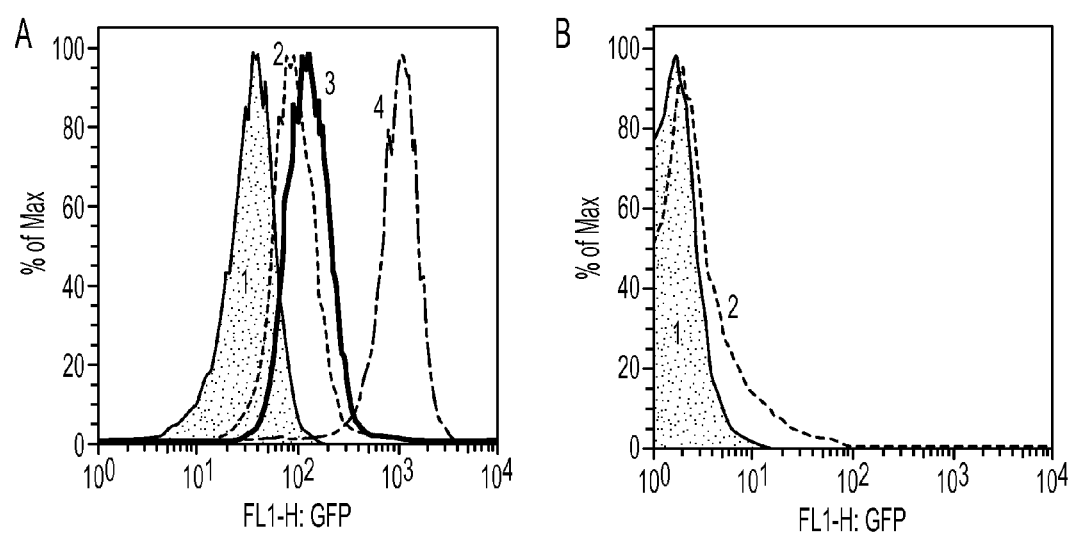
FIG. 14: Cell surface receptor binding of CD3-targeted and non-targeted protein nanostructures compared to the anti-CD3 monoclonal antibody in CD3+ HPB-MLT cells A) 1 (grey shading): untreated cells; 3: cells treated with 1 μM 7 (TG-13DDCD3); 2: cells treated with 1 μM 8 (TG-1DDCD3); 4: cells treated with FITC labeled anti-CD3 monoclonal antibody. B) 1 (grey shading): untreated cells; 2: cells treated with non-targeted nanostructures assembled with 13DD and 6 (TG-13DD, 0.4 μM).
Figure 15:
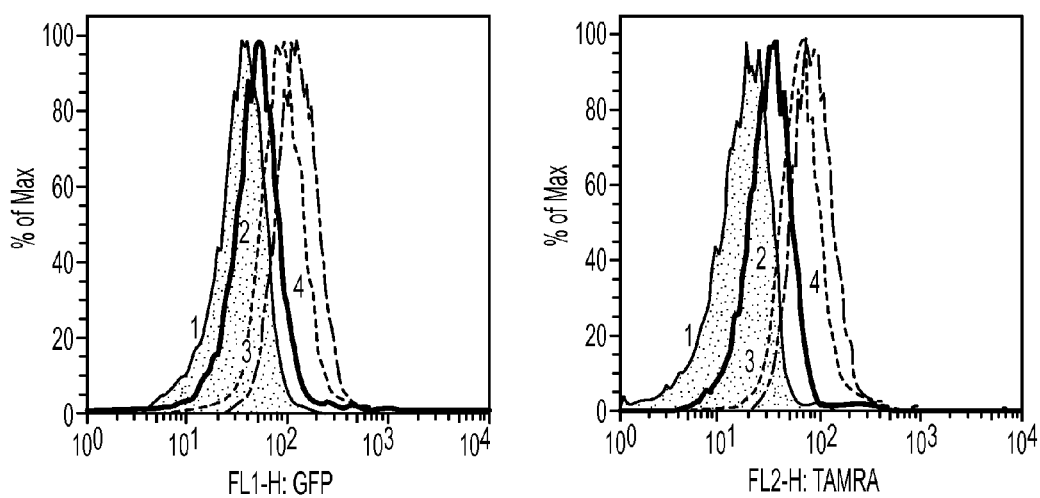
FIG. 15: Determination of CD3-specific binding of the assembled protein nanostructures to the HPB-MLT CD3 receptors (Left: GFP channel, Right: TAMRA channel). 1 (grey shading): untreated HPB-MLT cells; 2: HPB-MLT cells treated with 1 μM bisMTX-GFP-TAMRA (6); 3: HPB-MLT cells treated with 1 μM 8 (TG-1DDCD3); 4: HPB-MLT cells treated with 1 μM 7 (TG-13DDCD3).
Figure 16:
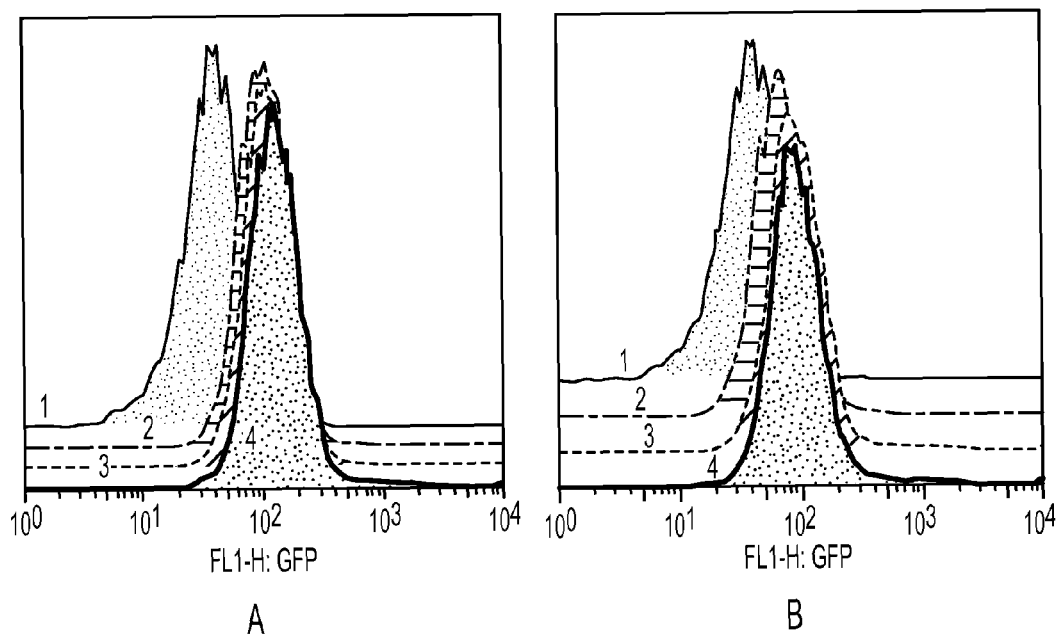
FIG. 16: Determination of the dose dependent CD3 receptor binding of assembled protein nanostructures (GFP channel); A) HPB-MLT cells treated with increasing concentrations of 7 (TG-13DDCD3) and B) with 8 (TG-1DDCD3) (1: untreated; 2: 0.1 μM; 3: 0.5 μM; 4: 1 μM).
Figure 17:
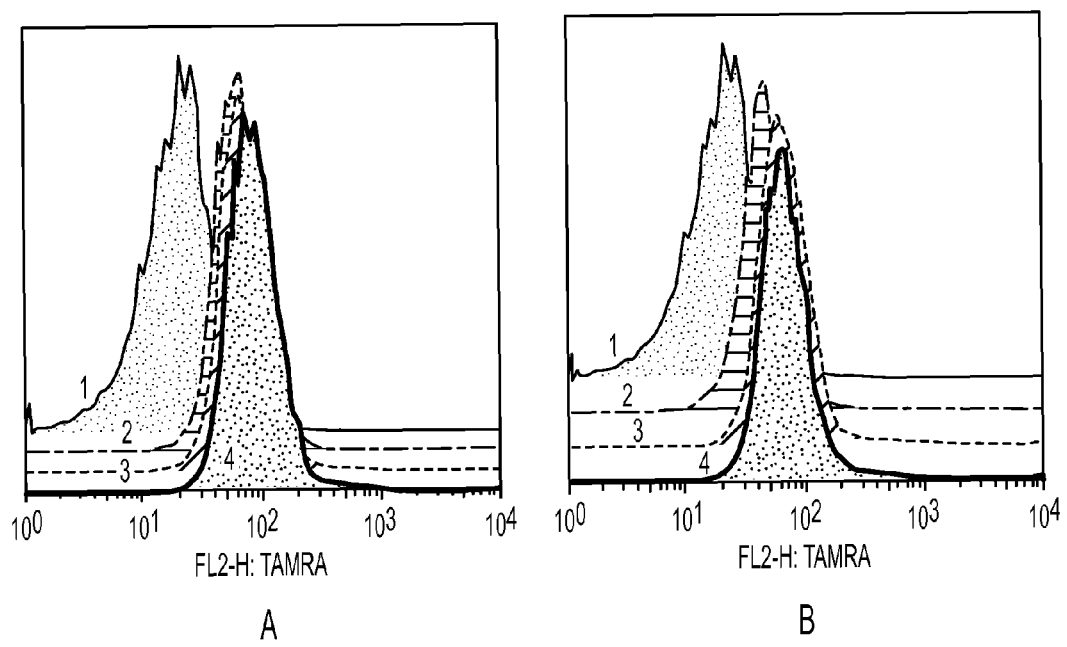
FIG. 17: Determination of the dose dependent CD3 receptor binding of assembled protein nanostructures (GFP channel); A) HPB-MLT cells treated with increasing concentrations of 7 (TG-13DDCD3) and B) with 8 (TG-1DDCD3) (1: untreated; 2: 0.1 μM; 3: 0.5 μM; 4: 1 μM).
Figure 18:
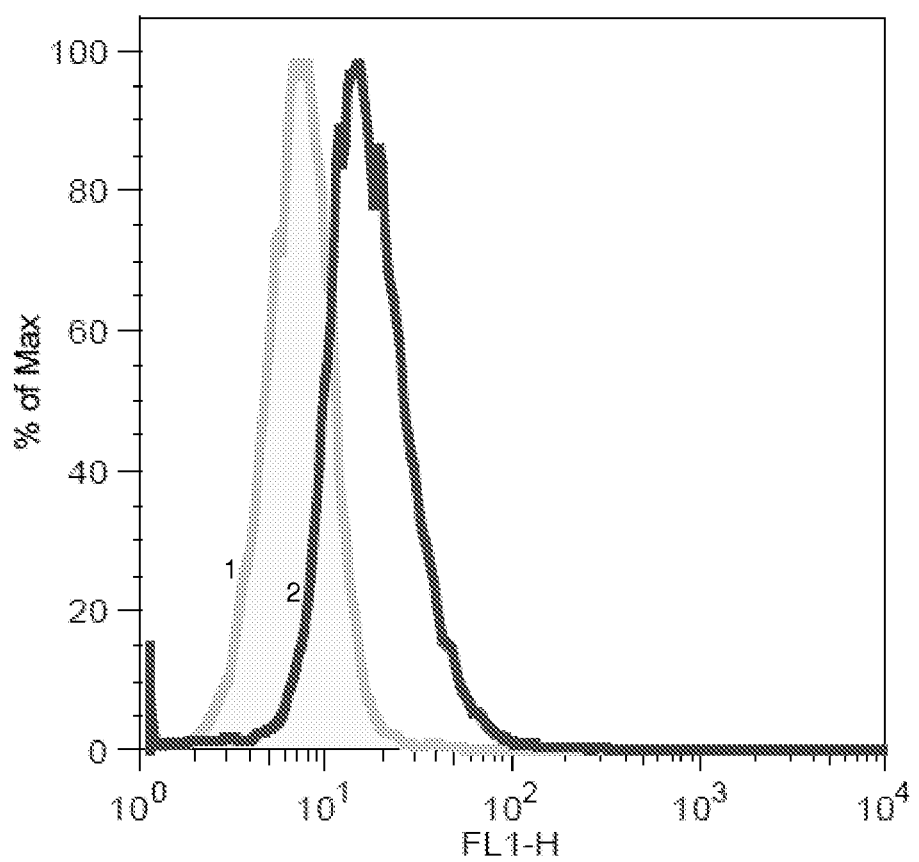
FIG. 18: Determination of the binding specificity of the assembled protein nanostructures: CD3 negative Daudi B cells were with treated with 1 μM 7 (TG-13DDCD3) (1: untreated cells; 2: 7 (TG-13DDCD3) treated CD3− Daudi B lymphoma cells at 4° C. (2 h)).
Figure 24:
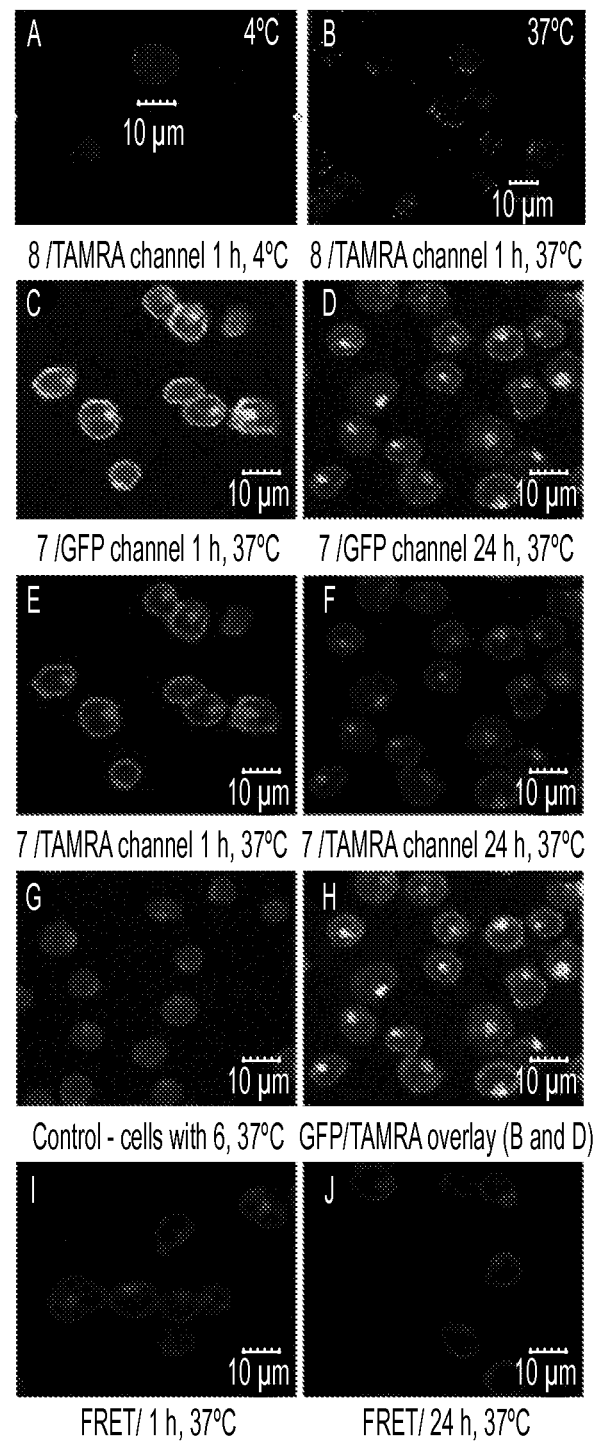
FIG. 24: (A and B) Internalization studies of TAMRA-GFP-1DDCD3 (8) with HPB-MLT T-leukemia cells at either 4° C. (Left) or 37° C. (Right). Cells were treated for 1 h. Images indicate red punctate structures on the cell membrane at 4° C. (Left) or within the cell at 37° C. (Right) (TAMRA channel). Magnification: 60×. (C to J) Internalization studies of TAMRA-GFP-13DDCD3 (7) with HPB-MLT T-leukemia cells at 37° C. (C and E) 7 incubated with CD3+ T-leukemia cells for 1 h [C: DAPI and GFP channels; E: TAMRA channel]; (D and F) 7 incubated with CD3+ T-leukemia cells for 24 h [D: DAPI and GFP channels; F: TAMRA channel]. (G) HPB-MLT cells treated with bis-MTX-GFP-TAMRA (6) for 1 h (control, blue=DAPI nuclear stain); (H) Overlay of the GFP and TAMRA channels indicate the intact assembled protein (co-localized yellow punctate); (I and J) FRET between GFP and TAMRA was observed by exciting the cells with 488 nm laser and a BA560/620 nm emission filter.
Figure 26:
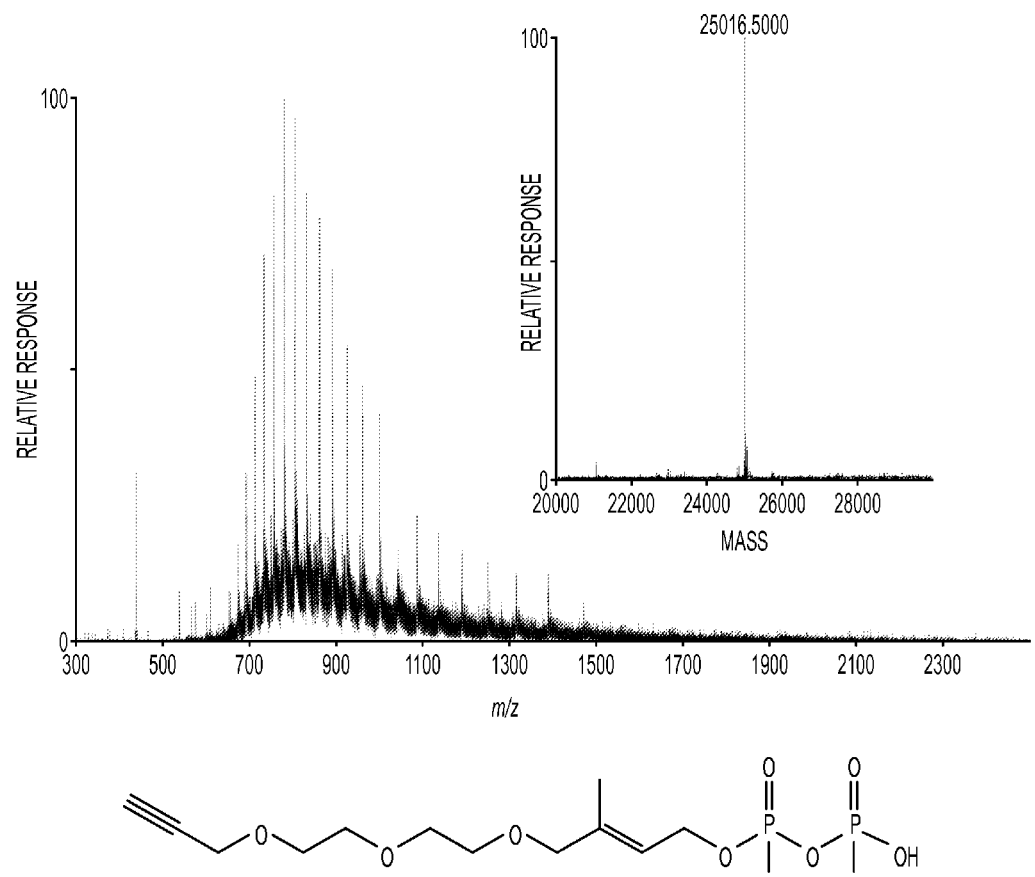
FIG. 26: ESI-MS analysis with the deconvoluted mass spectrum of CNTF-CVIA (SEQ ID NO: 1) prenylated with the long version of the FPP PEG analogue. The molecular mass calculated with 25,016.5 kDa and the mass found was 25,016.5000 kDa.
Figure 27:
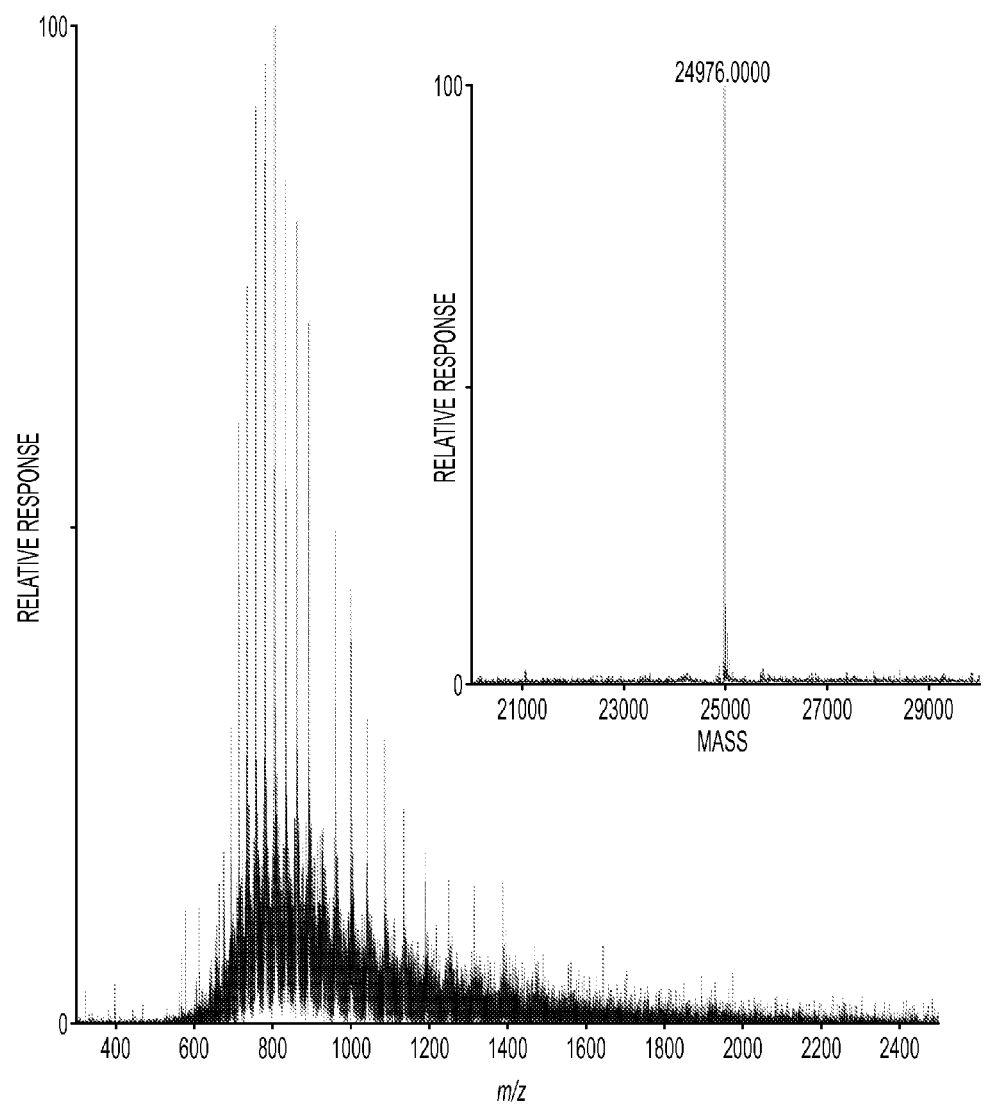
FIG. 27: ESI-MS analysis with the deconvoluted mass spectrum of CNTF-CVIA (SEQ ID NO: 1) prenylated with the short version of the FPP PEG analogue. The molecular mass calculated with 24,972.5 kDa and the mass found was 25,976.0000 kDa.
Figure 27:
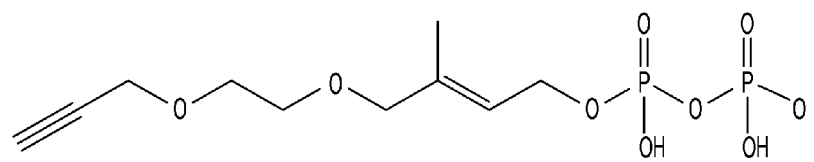

In another embodiment, $R_1$ is an antibody fragment. In another embodiment, $R_1$ is a non-antibody protein. In another embodiment, $R_1$ is a fibronectin scaffold manifesting antibody-like features. In another embodiment, $R_1$ is a peptide fragment. In an embodiment, the protein $R_1$ binds to a diagnostic marker. In an embodiment of the invention, the protein $R_1$ is therapeutically active. In an embodiment, the protein $R_1$ binds to an antigen. In an embodiment, the antigen is preferentially expressed on cancer cells. In an embodiment, the antigen is preferentially expressed on immune cells. In a particular embodiment, the protein may be Ciliary Neurotrophic Factor, Erythropoietin (EPO), Insulin-Like Growth Factor (IGF), Gastric Inhibitory Peptide, Ricin or Cholera Toxin. In a particular embodiment, the protein is Ciliary Neurotrophic Factor which is a protein encoded by the CNTF gene is a polypeptide hormone and nerve growth factor whose actions have been studied in the nervous system where it promotes neurotransmitter synthesis and neurite outgrowth in certain neural populations including astrocytes. The protein is a potent survival factor for neurons and oligodendrocytes and may be relevant in reducing tissue destruction during inflammatory attacks. Accordingly, the compounds of formula I may be used to modify the properties of Ciliary Neurotrophic Factor to make it more suitable for administration to a patient in need thereof. For example, the protein may be modified with a PEG group to prolong its half-life.

In methods of the invention, the protein to be modified contains a CaaX moiety, alternatively referred to herein as a CaaX box or CaaX sequence. The CaaX moiety is an amino acid sequence that is a substrate for farnesyltransferase and geranylgeranyltransferase I enzymes. Farnesyltransferase and geranylgeranyltransferase I are very similar proteins consisting of two subunits, the a-subunit, which is common to both enzymes, and the β-subunit, whose sequence identity is just 25%. These enzymes recognize the CaaX box at the C-terminus of the target protein. "C" is the cysteine residue that is prenylated, "a" is any aliphatic amino acid, and the identity of "X" determines which enzyme acts on the protein. Farnesyltransferase recognizes CaaX boxes where X =M, S, Q, A, or C, whereas geranylgeranyltransferase I recognizes CaaX boxes with X=L or E. The CaaX moiety may be appended to the protein by a chemical linker or else introduced recombinantly, i.e. by inserting a CaaX encoding nucleic acid sequence into the nucleic acid coding region expressing the protein. In a particular embodiment, the CaaX moiety is CVIA (SEQ ID NO: 1 and the enzyme is farnesyltransferase.

Self-organization of protein molecules into higher order structures is an integral part of living cells. Unlike DNA and RNA based nanostructures,[35-38] the rules governing protein self-assembly are only beginning to be defined. Much of the previous effort to construct biomimetic protein assemblies has been based on direct protein-protein interactions through the incorporation of complementary amino acid residue surface interactions.[39] As an alternative, chemical biological approaches for macromolecular protein assembly based on metal coordination,[40] polymer conjugation[41], enzyme-inhibitor interactions,[42-44] and chemically induced dimerization[45] have begun to be explored.

In previous work we reported on the design of chemically self-assembled nanoring structures (CSANs) constructed from dimeric forms of dihydrofolate reductase (DHFR) and bis-methotrexate (bis-MTX).[46] Upon mixing, the two components spontaneously assemble into a mixture of compact rings and polymeric structures that can be readily separated by size exclusion chromatography. The ring structures have been studied by dynamic light scattering, TEM and AFM and it has been shown that the number of DHFR and MTX dimers in the ring can be controlled by the length of the linker region that joins the two DHFR monomers; due to the high affinity of MTX for DHFR d, the cyclic forms resist linearization in the absence of an exogenous inhibitor of DHFR.[46,47] The CSANS are highly stable exhibiting Tm values between 62° C. and 65° C. (unpublished observation). The utility of the nanorings has been expanded to incorporate single chain antibodies (scFvs) and peptides, thus allowing them to be targeted to cell surface receptors. In particular, we have previously demonstrated that anti-CD3 scFV-DHFR$^2$ fusion proteins containing a 13 amino acid linker or a one amino acid linker will self assemble in the presence of a bis-MTX into bivalent and octavalent anti-CD3 CSANS, respectively. Further, we have demonstrated that the anti-CD3 CSANS bind specifically to $CD3^+$ T-leukemia cells with dissociation constants comparable to the parental monoclonal antibody, ($K_d$, UCHT-1 MAB=1.8 nM; $K_d$, bivalent anti-CD3 CSANS=3.5 nM, Kd octavalent anti-CD3=0.93 nM). In addition, the anti-CD3 CSANs undergo rapid clathrin dependent endocytosis by T-leukemia cells, which enables drug or oligonucleotide delivery.[28,47-49] To demonstrate the ability of the CSANs to carry out protein delivery, we decided to explore the use of the dual labeling strategy reported here to link the bis-MTX element to a protein. Accordingly, we designed and prepared anti-CD3-CSANs capable of delivering a protein cargo into T-leukemia cells. Thus, bis-MTX-GFP-TAMRA, 6, was prepared. A previously reported amino-bis-MTX trilinker[48] (S16) was coupled to 5-azidopentanoic acid using standard peptide chemistry to obtain azido-bis-MTX, S14. Next, the bifunctional prenylated protein 4 described above was incubated with aminooxy-TAMRA, S15, and azido-bis-MTX, S14, for 15 h using the optimized reaction conditions (vide supra). Subsequent LC-MS analysis of the reaction mixture revealed the successful simultaneous conjugation of the protein with both aminooxy-TAMRA and azido-bis-MTX (FIG. 22). Overall, the conjugation reactions appear to be highly efficient, since little free starting material was observed by LC-MS; the high efficiency seen in this case is similar to results noted above for other GFP and CNTF conjugates. With the bis-MTX- and TAMRA-functionalized GFP-protein (6) in hand, we then evaluated the chemically induced self-assembly of this protein with dimeric DHFR (DD) proteins by HP-SEC. After simple mixing of the two entities and incubation at rt for 2 h, the samples were analyzed by HP-SEC. The elution profiles of the HP-SEC chromatograms indicated the predominant formation of the internal monomeric species with 13-DHFR-DHFR (13DD) and a much higher order species with 1-DHFR-DHFR (1DD, FIG. 10-11). Note that in this nomenclature system, 13DD is single polypeptide chain incorporating two DHFR domains separated by a 13 residue spacer whereas 1DD is a similar dimer separated by a one residue spacer.[28] Having confirmed the self-assembly with non-targeting DHFR proteins, we then moved to construct the TAMRA-GFP-DD-antiCD3 protein nanostructures by mixing 13DD-antiCD3 (13DDCD3) and 1DD-antiCD3 (1DDCD3) with 6. These latter DHFR-based constructs are similar to 13DD and 1DD with the exception that they each have a single chain antibody (antiCD3) fused to the C-terminus of the DHFR dimer; the presence of the antiCD3 moiety allows these constructs to be targeted to cells displaying the CD3 antigen. The assemblies containing the targeting proteins generated a similar pattern in the SEC profile compared with the constructs prepared from DHFR dimers lacking the antiCD3 domain (FIG. 23).

Consistent with what was observed with the corresponding non-targeting DHFR proteins, TAMRA-GFP-DDCD3 CSANs prepared with 13DDCD3 (7), exhibited predominantly internal monomer, dimers and small amounts of higher order species. The species eluting between 20-22.5 min (7) were collected, concentrated by ultrafiltration and their final concentration was determined based on the collected peak area. This material was used for cellular internalization studies (FIG. 24). Similar SEC experiments and cell internalization experiments were performed with assemblies prepared from 1DDCD3 as well which gave similar results to those obtained with 13DDCD3 (FIGS. 12 and 13).

In order to study the functionality of the TAMRA-GFP 13- and 1-DDCD3 CSANs (7 and 8, respectively), we evaluated their ability to specifically deliver the protein nanostructure to CD3$^+$ T-leukemia cells. The cells were incubated with 7 for 1 h (at 4° C. and 37° C.) and evaluated by confocal laser scanning microscopy for cellular internalization. Both the GFP and TAMRA chromophores were excited individually to observe the GFP and TAMRA emission.

Additionally, FRET was observed between the two fluorophores when GFP was excited and TAMRA emission was monitored. First, control experiments in which CD3$^+$ T-leukemia cells were treated only with the GFP-TAMRA conjugate, 6, showed minimal fluorescence (FIG. 24G). In addition, no significant binding to CD3$^+$ T-leukemia cells by CSANs prepared with 6 was observed by FACS. (FIG. S15) Confocal microscopy imaging confirmed the delivery of the nanostructures (7 and 8) into the cells via an energy dependent endocytic process (FIG. 24 and FIGS. 12-13). At 4° C., TAMRA fluorescence was observed on the cell membranes, (FIG. 24A) and at 37° C. distinct punctate structures (FIG. 24B) were observed within the cells indicating the energy dependent uptake of both GFP and TAMRA. Overlay of the GFP/TAMRA channels indicated that the two fluorophores were present in the same location (FIG. 24H), while the positive FRET signal was consistent with the GFP/TAMRA conjugate, 6, having remained intact in the cells during the time period of the experiment (24 h) (FIGS. 24I and 24J). The observed temperature dependent uptake of nanostructures at 37° C. and the punctate structures are consistent with our previous observations with antiCD3 scFv CSANs.[28]

The invention further provides pharmaceutical compositions comprising a compound of formula III and a pharmaceutically acceptable carrier. Administered of the composition to a mammalian host, such as a human patient may be in a variety of forms adapted to the chosen route of administration, i.e. parenterally, orally, intranasally, rectally or inhaled. Typically, compositions of the invention will be administered parenterally, such as by intravenous or subcutaneous injection or infusion but may also be administered in an implantable device. The composition may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the compound of formula III may be combined with one or more excipients and used in the form of ingestible tablets, buccal tablets, troches, capsules, elixirs, suspensions, syrups, wafers, and the like. Such compositions and preparations should contain at least 0.1% of the compound of formula III. The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The composition can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations may contain a preservative to prevent the growth of microorganisms. The pharmaceutical dosage forms can include sterile aqueous solutions or dispersions or sterile powders comprising the compound of formula III optionally encapsulated in liposomes. In all cases, the ultimate dosage form may be sterile, fluid and stable under the conditions of manufacture and storage. The liquid carrier or vehicle may be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile solutions are prepared by incorporating the compound of formula III in the required amount in the appropriate solvent with various of the other ingredients enumerated above, as required, followed by filter sterilization. In the case of sterile powders for the preparation of sterile solutions, the preferred methods of preparation are vacuum drying and the freeze drying techniques, which yield a powder of the compound of formula III plus any additional desired ingredient present in the previously sterile-filtered solutions.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied to devices such as absorbent pads, used to impregnate bandages and other dressings.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the composition can be determined by comparing the in vitro activity, and in vivo activity of the pharmaceutically active compound in animal models. Methods for the extrapolation of effective dosages in mice, and other animals, to humans are known to the art; for example, see U.S. Pat. No. 4,938,949.

The amount of the composition required for use in treatment will vary with the route of administration, the nature of the condition being treated and the age and condition of the patient and will be ultimately at the discretion of the attendant physician or clinician. The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator.

EXAMPLES

Abbreviations:
 Bis-MTX, bis-methotrexate;
 DMF, dimethylformamide;
 DTT, dithiothreitol;
 EDTA, Ethylenediaminetetraacetic acid;
 ESI-MS, electrospray ionization mass spectrometry;
 FPP, Farnesyl diphosphate;
 GFP, green fluorescent protein;
 mPDA, m-phenylenediamine;
 PB, phosphate buffer;
 PFTase, protein farnesyl transferase;
 RP-HPLC, reversed-phase high-pressure liquid chromatography;
 SEC, size exclusion chromatography;
 TEA, triethylamine; and
 Tris, tris(hydroxymethyl)aminomethane.
General:

All synthetic reactions were carried out at rt and stirred magnetically unless otherwise noted.

TLC was performed on precoated (250 mm) silica gel 60 F-254 plates (Merck). Plates were visualized by staining with $KMnO_4$ or with a hand-held UV lamp. Flash chromatography was performed using a Biotage® instrument. Deuterated NMR solvents were purchased from Cambridge Isotope Laboratories, Inc. $^1$H NMR spectra were obtained at 500 MHz; $^{13}$C NMR spectra were obtained at 125 MHz. All NMR spectra were acquired on Varian instruments at 25° C. Chemical shifts are reported in ppm and J values are in Hz. Fluorescence assay data were obtained using a Varian Cary Eclipse Fluorescence Spectrophotometer. MS spectra for synthetic reactions were obtained on a Bruker BioTOF II instrument. Yeast PFTase was prepared as previously described.[50] Protein LC/MS analyses were performed using a Waters Synapt G2 Quadropole TOF mass spectrometer instrument. MALDI-MS analyses were performed with a Bruker MALDI TOF spectrometer Instrument. Preparative HPLC separations were performed by using a Beckman model 127/166 instrument, equipped with a UV detector and a Phenomenex $C_{18}$ column (Luna, 10 μm, 10×250 mm). Vydac 218TP1010 column was used for preparative RP-HPLC. Size Exclusion Chromatography (SEC) was performed on a System Gold 126/168 HPLC system (Beckman-Coulter, Fullerton, Calif., USA) connected to a Superdex G75 or G200 column (GE Healthcare Life sciences) with P500 buffer (0.5 M NaCl, 50 mM $KH_2PO_4$, 1 mM EDTA, pH 7) as the mobile phase (flow rate 0.5 mL/min). All solvents were of HPLC grade. Aminooxy-PEG (3 kDa) S12 was purchased from Quanta Biodesign Inc. All other reagents were from Sigma Aldrich.

Example 1

5-formyl-1,3-phenylene bis(trifluoromethanesulfonate) (S2)

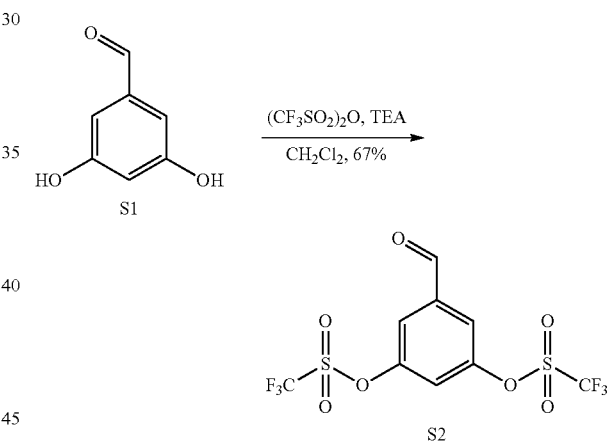

Compound S2 was synthesized according to modified literature procedures.[51, 52] Under $N_2$, 3,5-dihydroxy-benzaldehyde (2.00 g, 14.5 mmol, 1.0 eq) was dissolved in $CH_2Cl_2$ (20 mL) and TEA (43.4 mmol, 6.05 mL, 4.4 g). The mixture was cooled in an ice bath at 0° C. and a solution of $(CF_3SO_2)_2O$ (8.9 g, 31.5 mmol, 2.2 eq) in $CH_2Cl_2$ (10 mL) was added dropwise. The reaction mixture was stirred for another 2 h and allowed to warm up to rt during this period. $H_2O$ (50 mL) was added and the product was extracted with $CH_2Cl_2$ (2×30 mL). The combined organic layers were washed with 1 M HCl (30 mL), $H_2O$ (30 mL) and brine (20 mL), dried over $Na_2SO_4$ and then the solvent was removed in vacuo. The brown residue was purified by silica gel flash column chromatography (Hex/EtOAc 4:1) to yield S2 (3.86 g, 67%) as a slightly yellowish powder. $^1$H NMR (δ, $CDCl_3$): 10.021 (s, 1H), 7.845 (d, J=2.0 Hz, 2H), 7.484 (t, J=2.2 Hz, 1H). $^{13}$C NMR (δ, $CDCl_3$): 187.527, 158.932, 150.049, 121.983, 120.774, 117.337.

Example 2

3-formyl-5-(((trimethylsilyl)ethynyl)phenyl trifluoromethanesulfonate (S3)

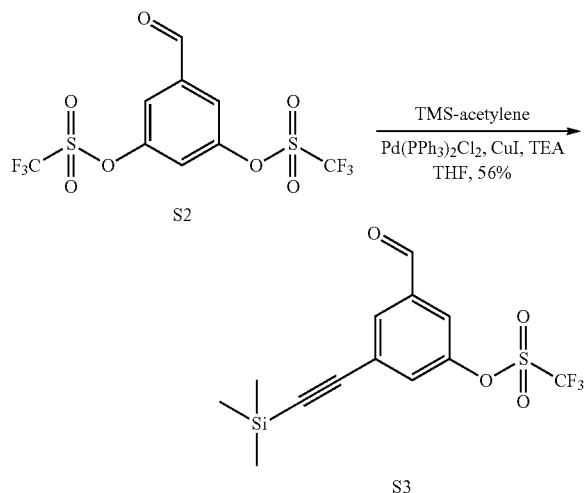

Compound S3 was synthesized according to modified literature procedures.[51, 52] Compound S2 (3.6 g, 8.95 mmol, 1.0 eq) was dissolved in THF (40 mL) and TEA (20 mL). Pd(PPh$_3$)$_2$Cl$_2$ (63.5 mg, 0.09 mmol, 0.01 eq) and CuI (34.7 mg, 0.18 mmol, 0.02 eq) were added to the reaction mixture. The mixture was cooled in an ice bath at 0° C. and a solution of TMS-acetylene (1.27 mL, 8.95 mmol, 1.0 eq) in THF (20 mL) was slowly added dropwise. The reaction was monitored by TLC. The mixture was stirred for another 2 h during which time the temperature was allowed to rise to rt. The solvents were removed in vacuo and sat. NH$_4$Cl (30 mL) and EtOAc (50 mL) were added. The layers were partitioned and the aqueous layer was extracted with EtOAc (50 mL) The combined organic layers were washed with H$_2$O (50 mL) and brine (50 mL), dried over Na$_2$SO$_4$ and solvent was removed in vacuo. Purification by silica gel flash column chromatography (Hex/EtOAc 30:1) gave S3 (1.72 g, 4.9 mmol, 55.5%) as a colorless oil. $^1$H NMR (δ, CDCl$_3$): 9.965 (s, 1H), 7.948 (d, J=1.0 Hz, 1H), 7.692 (dd, J=1.0, 1.0 Hz, 1H), 7.564 (dd, J=1.0, 1.5 Hz, 1H), 0.254 (s, 9H). $^{13}$C NMR (δ, CDCl$_3$): 189.185, 149.601, 138.101, 133.285, 129.713, 120.926, 100.941, 99.540, 79.803, 68.189, −0.383.

Example 3

3-ethynyl-5-hydroxybenzaldehyde (S4)

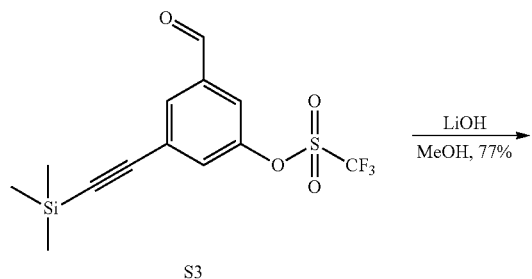

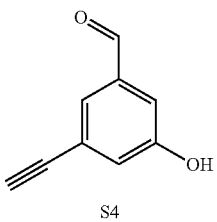

Compound S4 was synthesized according to modified literature procedures.[51, 52] S3 (1.7 g, 4.85 mmol, 1.0 eq) was dissolved in MeOH (15 mL). A solution of LiOH (1.0 g, 23.8 mmol, 5 eq) in MeOH (15 mL) was added at 0° C., and next the temperature was allowed to rise to rt overnight. The mixture was then extracted with Et$_2$O (3×15 mL) and the combined organic layers were washed with H$_2$O (10 mL) and brine (10 mL) and dried over Na$_2$SO$_4$. The solvent was removed in vacuo and purification by silica gel flash column chromatography (Hex/Et$_2$O 2:1) gave S4 (0.55 g, 77%) as a white powder. $^1$H NMR (δ, CDCl$_3$): 9.895 (s, 1H), 7.537 (dd, J=1.5, 1.5 Hz, 1H), 7.336 (dd, J=1.0, 1.0 Hz, 1H), 7.213 (dd, J=1.0, 1.0 Hz, 1H), 6.094 (s, 1H), 3.126 (s, 1H); $^{13}$C NMR (δ, CDCl$_3$): 191.476, 156.345, 137.802, 127.061, 124.955, 115.343, 113.589, 81.798, 78.762.

Example 4

3-(((2E,6E)-2,6-dimethyl-8-((tetrahydro-2H-pyran-2-yl)oxy)octa-2,6-dien-1-yl)oxy)-5-ethynylbenzaldehyde (S8)

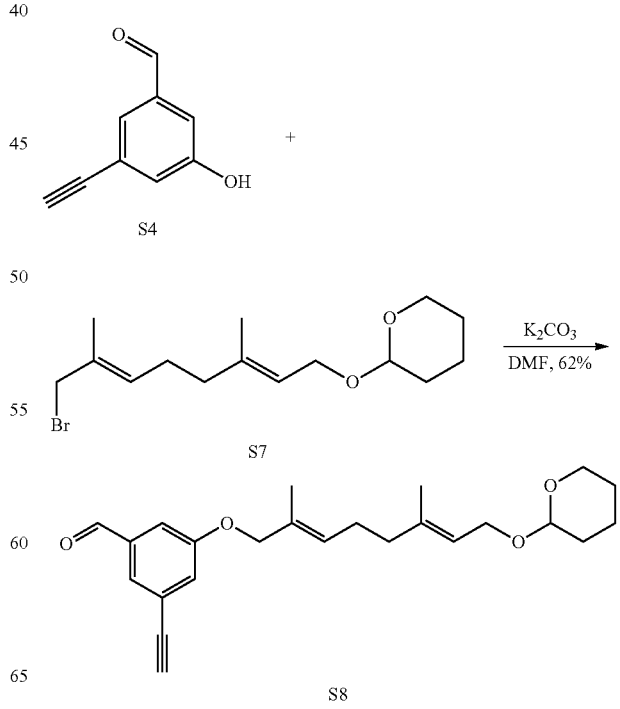

Compounds S5, S6 and S7 were prepared as previously described.[53, 54] Bromide S7 (0.036 g, 1.136 mmol) and S3 (0.292 g, 2.0 mmol) were dissolved in DMF (15 mL) in a flame dried 50 mL flask. $K_2CO_3$ (0.50 g, 3.62 mmol) was added to the reaction flask, then left to stir at 100° C. for 3 h until TLC analysis (2:1 Hex:EtOAc v/v) indicated almost complete conversion to the product. The solvent was removed in vacuo and the crude product was further purified by silica gel column chromatography with gradient elution (Hex:Et$_2$O) from 1:0 (v/v) going to 5:1 (v/v) to afford 0.27 g of compound S8 (0.7 mmol, 62% yield) as a pale yellow oil. $^1$H NMR (500 MHz, CDCl$_3$) δ 9.910 (s, 1H), 7.542 (dd, J=1.0 Hz, 1H), 7.373 (dd, J=1.0 Hz, 1H), 7.265 (dd, J=1.0 Hz, 1H), 5.538 (t, J=7.0 Hz, 1H), 5.357 (t, J=6.5 Hz, 1H), 4.610 (m, 1H), 4.420 (s, 2H), 4.235 (dd, J=9.5, 6.5 Hz, 2H), 4.004 (m, 1H), 3.95-3.83 (m, 1H), 3.495 (m, 1H), 3.135 (s, 1H) 2.201 (m, 2H), 2.081 (t, J=7.5 Hz, 2H), 1.714 (s, 3H), 1.671 (s, 3H), 1.66-1.46 (m, 5H). $^{13}$C NMR (125 MHz, CDCl$_3$) δ 191.132, 159.165, 139.845, 139.436, 137.626, 130.257, 129.160, 127.406, 126.765, 124.698, 120.982, 114.326, 97.817, 82.006, 78.458, 63.552, 62.238, 38.865, 30.639, 25.905, 25.417, 19.552, 16.350, 13.779. HR-ESI-MS calcd for $C_{24}H_{30}O_4Na$ [M+Na]$^+$ 405.2037, found 405.2051.

Example 5

3-ethynyl-5-(((2E,6E)-8-hydroxy-2,6-dimethylocta-2,6-dien-1-yl)oxy)benzaldehyde (S9)

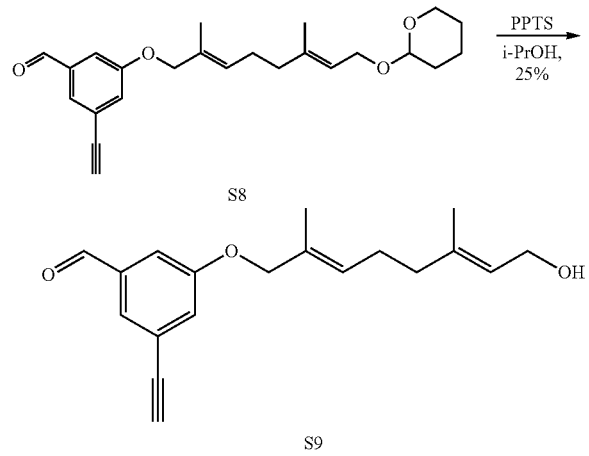

Protected alkyne-aldehyde S8 (0.25 g, 0.65 mmol) was dissolved in i-PrOH (15 mL) in a 25 mL flask. PPTS (10 mg) was added as catalyst. The reaction was then refluxed at 75° C. for 4 h, when TLC analysis indicated complete conversion to the product. It was then quenched by adding sat. NaHCO$_3$ (5 mL) and EtOAc (50 mL) The organic layer was then separated and dried over Na$_2$SO$_4$. The solvent was removed in vacuo and afforded 49 mg of compound S9 (25% yield) as a pale yellow oil. $^1$H NMR (500 MHz, CDCl$_3$) δ 9.901 (s, 1H), 7.536 (dd, J=1.0 Hz, 1H), 7.365 (dd, J=1.0 Hz, 1H), 7.257 (dd, J=1.0 Hz, 1H), 5.519 (t, J=7.0 Hz, 1H), 5.386 (t, J=6.5 Hz, 1H), 4.419 (s, 2H), 4.126 (d, J=7.0, 2H), 3.115 (s, 1H) 2.195 (m, 2H), 2.064 (t, J=7.0 Hz, 2H), 1.701 (s, 3H), 1.657 (s, 3H). $^{13}$C NMR (125 MHz, CDCl$_3$) δ 191.476, 156.345, 139.640, 141.820, 137.802, 127.061, 124.955, 124.481, 115.343, 113.573, 81.798, 80.220, 78.762, 68.229, 65.987, 27.067, 22.822, 15.116, 14.676.

Example 6

(2E,6E)-8-(3-ethynyl-5-formylphenoxy)-3,7-dimethylocta-2,6-dien-1-yl diphosphate (1)

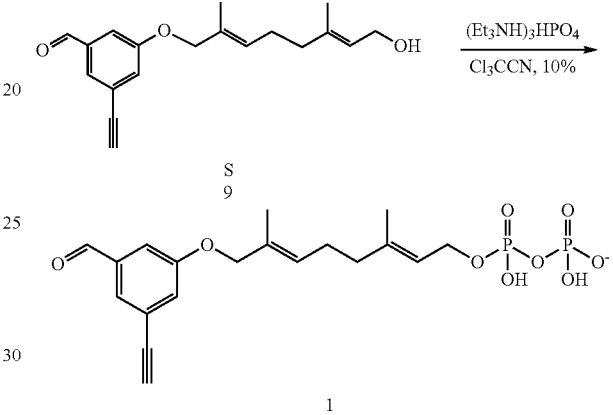

Alcohol S9 (25 mg, 0.084 mmol, 1 eq) was added to CCl$_3$CN (50.5 uL, 0.5 mmol, 6 eq) in a 25 mL flask. In a separate 5 mL flask, (Et$_3$NH)$_2$HPO$_4$ salt (0.25 mmol, 75.6 mg, 3 eq) was added to dry CH$_3$CN (3 mL), and placed in an oil bath at 30° C. for 5 min to dissolve the salt. This solution was added drop-wise to the mixture of alcohol S9 and CCl$_3$CN solution over 3 h at rt, and was left to stir for an additional 50 min at rt. The slow addition of salt solution to the reaction flask was critical to significantly increase the yield. The solvent was removed in vacuo and NH$_4$HCO$_3$ (25 mM, 5 mL) was added to the resulting solution and a white precipitate was formed. The solution was filtered and purified by RP-HPLC with a semi-preparative column under the following conditions: detection at 254 nm; flow rate at 5.0 mL·min$^{-1}$; 5 mL injection loop; solvent A: 25 mM NH$_4$HCO$_3$ in H$_2$O, solvent B: CH$_3$CN. compound 1 eluted from 20-25% solvent B. Fractions containing pure 1 were collected and lyophilized. The resulting salt was dissolved in D$_2$O and its concentration was measured following a previously established NMR-based quantification[5] to yield 4 mL of 2.0 mM solution of 1 (3.84 mg, 10% yield). $^1$H NMR (500 MHz, CDCl$_3$) δ 9.712 (s, 1H), 7.549 (dd, J=1.0 Hz, 1H), 7.371 (dd, J=1.0 Hz, 1H), 7.297 (dd, J=1.0 Hz, 1H), 5.458 (t, J=7.0 Hz, 1H), 5.265 (t, J=7.0 Hz, 1H), 4.432 (s, 2H), 4.279 (d, J=6.5, 2H), 3.436 (s, 1H) 2.077 (m, 2H), 1.947 (t, J=7.5 Hz, 2H), 1.553 (s, 3H), 1.532 (s, 3H). $^{31}$P NMR: (121 MHz, D$_2$O) δ −6.465 (d, J=17.2, 1P), −3.505 (d, J=16.5, 1P). HR-ESI-MS calcd for $C_{15}H_{26}O_8P_2$ [M-H]$^-$ 395.1025, found 395.0907.

Example 7
Synthesis of Azido-bisMTX (S14)
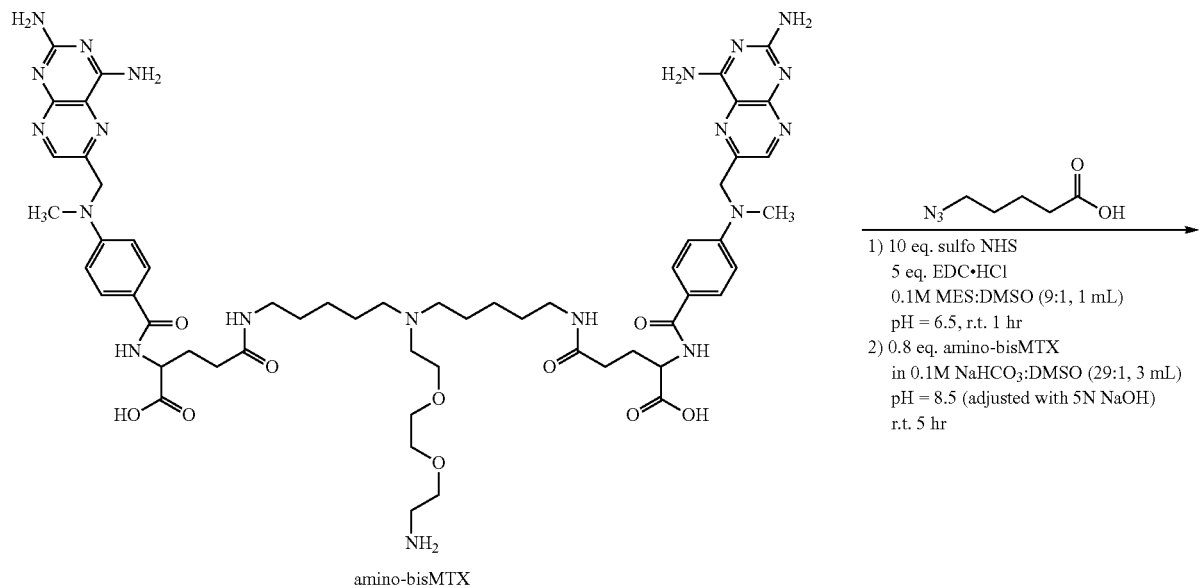
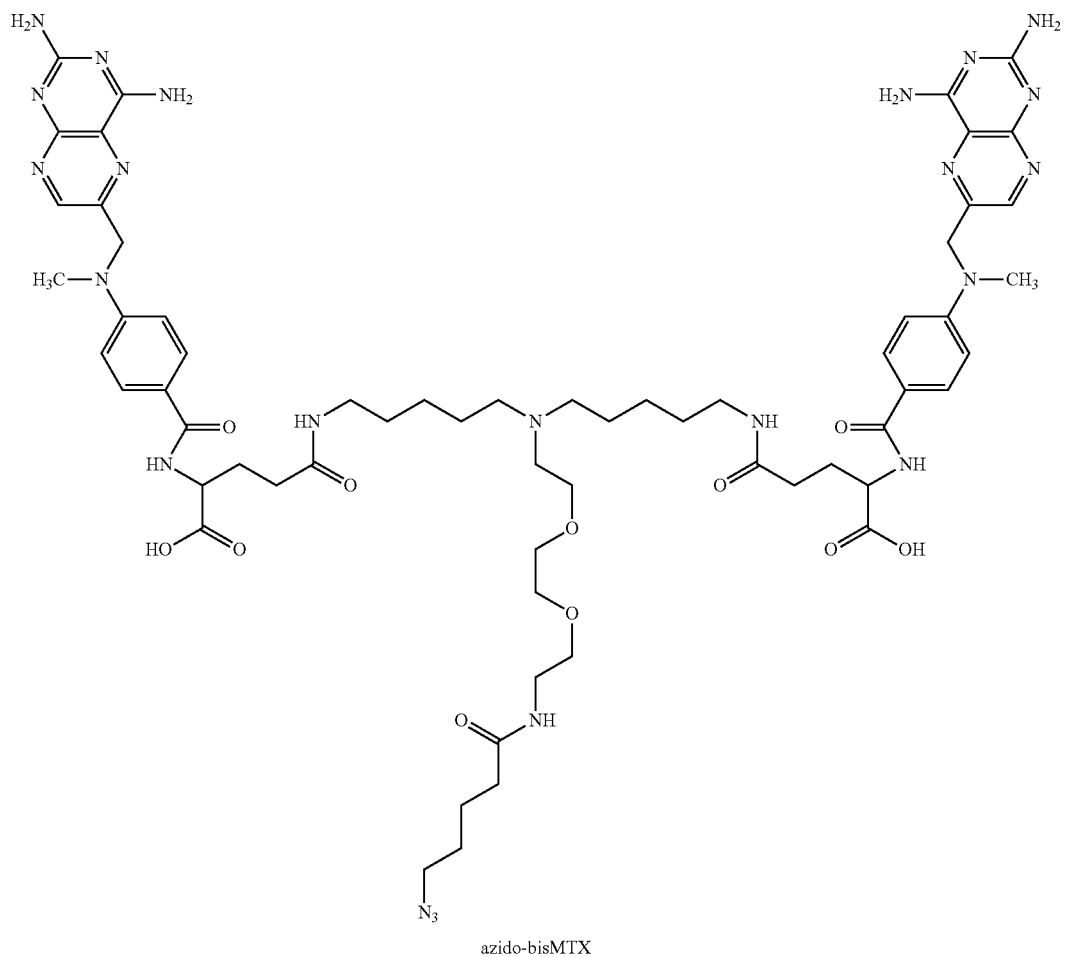

To a solution of N-hydroxysulfosuccinimide (43.4 mg, 200 µmol) and 1-ethyl-3-(3-dimethylaminopropyl)carbodiimide hydrochloride (EDC, 19.2 mg, 100 µmol) in 0.1 M MES buffer:DMSO (9:1, 1 mL) at pH 6.5 was added 5-azidopropionic acid (2.9 mg, 20 µmol) and the mixture was stirred for 1 h at rt followed by addition of amino-bisMTX[57] (19.1 mg, 16 µmol) in 0.1 M NaHCO$_3$:DMSO (29:1, 3 mL) to the reaction mixture. The reaction mixture was stirred at rt in the dark for 5 h. Next, the crude reaction mixture was purified by RP-HPLC using a C8-semi-preparative HPLC column with an H$_2$O/0.1% TFA and CH$_3$CN/0.1% TFA gradient. The reaction gave 12 mg (83%) of pure product. ESI-MS calcd for $C_{61}H_{85}N_{23}O_{11}$ $[M+3H]^{3+}$ 439.5599, found 439.4167.

Example 8

Enzymatic Studies of FPP-Analogue 1 Using Continuous Fluorescence Assay

Enzymatic reaction mixtures contained Tris.HCl (50 mM, pH 7.5), MgCl2 (10 mM), ZnCl2 (10 µM), DTT (5.0 mM), 2.4 µN-dansyl-GCVIA (SEQ ID NO: 2) (2), 0.040% (w/v) n-dodecyl-β-D-maltoside PFTase (80 nM), and varying concentrations of 1 (0-50 µM), in a final volume of 250 µL. The reaction mixtures were equilibrated at 30° C. for 1 min, initiated by the addition of PFTase, and monitored for an increase in fluorescence (λex=340 nm, λem=505 nm) for approximately 20 min. The initial rates of formation of products were obtained as slopes in IU/min using least squares analysis. Corrections were applied to all the rate calculations based on the difference between the fluorescence intensity of the prenylated product and the starting peptide. Assuming 100% conversion, the difference corresponds only to the fluorescence of the total amount of the product. The slope was then divided by the fluorescence difference followed by multiplying by the total concentration of peptide (2.4 µM) which then gives the rate of formation of product in µM/s. It should be noted that the KM values reported here are actually apparent KM values, since the measurements were performed in only a single peptide concentration. The data were fit to a Michaelis-Menten model $$\left(V = \frac{[E\circ]k_{cat} *[S]}{K_M + [S]}\right)$$

using a nonlinear regression program, to determine kcat and KM (FIG. 4).

Example 9

Enzymatic Incorporation of Compound 1 into GFP-CVIA (SEQ ID NO: 1) (3)[27]

Enzymatic reaction mixtures (10 mL) contained Tris.HCl (50 mM, pH 7.5), MgCl2 (10 mM), KCl (30 mM), ZnCl2 (10 µM), DTT (5.0 mM), 7 (2.4 µM), compound 1 (30-50 µM), and PFTase (80-200 nM). After incubation at 30° C. for 4 h, the reaction mixture was concentrated using an Amicon Centriprep centrifugation device (10,000 MW cutoff). Next, excess of 1 was removed through a NAP-5 (Amersham) column using Tris.HCl (50 mM, pH 7.5) as the eluant. The subsequent protein concentration was calculated by UV absorbance at 488 nm (ε=55,000 M-1.cm-1).

Example 11

Coupling Bifunctionalized-GFP (4) with Aminooxy-Dansyl (S10)

Aminooxy-dansyl (S10) (3.2 µL of 10 mM solution in DMSO) was added to 42 µL of 4 (stock solution of 60 µM in 0.1 M Phosphate buffer pH 7.0). Phosphate buffer (1 M, pH 7.0, 2.5 µL) was added and the reaction was initiated by adding 40 mM m-phenylendiamine as a catalyst and was allowed to proceed for 2 h at rt. The mixture was then purified by a NAP-5 column to remove excess dye. LC-MS analysis of the sample showed only oxime-ligated protein and no free aldehyde was detected suggesting that the reaction had proceeded to completion. A gradient of 0-100% solvent A (H$_2$O, 0.1% HCO$_2$H) to B (CH$_3$CN, 0.1% HCO$_2$H) in 25 min was used for the LC-MS analysis.

Example 12

Coupling Bifunctionalized-GFP (4) with Azido-TAMRA (S11)

Azide-TAMRA (S11) (7 µL of 2.2 mM solution in DMSO) was added to 100 µL 4 (stock solution of 40 µM in PB). CuSO$_4$ (1 mM), TCEP (1 mM), TBTA (100 µM) were added and the reaction was allowed to proceed for 3 h. LC-MS analysis of the sample showed the presence of both the clicked protein 4a and the free alkyne-protein 4. The ratio of free alkyne-protein 4 to its respective clicked product 4a, was ~2, indicating only ~35% completion of click reaction had been achieved within this time and range of reactant concentrations. The reaction was repeated using 50% more azido-TAMRA S11 (225 µM) and was allowed to proceed for 16 h. LC-MS analysis of the reaction mixture showed >95% conversion of 4 to its respective clicked product 4a. A gradient of 0-100% solvent A (H$_2$O, 0.1% HCO$_2$H) to B (CH$_3$CN, 0.1% HCO$_2$H) in 25 min was used for the LC-MS analysis.

Example 13

Simultaneous Coupling Reaction Between Bifunctional-GFP 4 with Azido-TAMRA S11 and Aminooxy-dansyl S10

Azido-TAMRA (S11) (7 µL of 2.2 mM solution in DMSO) and aminooxy-dansyl (S10) (7 µL of 10 mM solution in DMSO) were added to 100 µL 4 (stock solution of 40 µM in PB). CuSO4 (1 mM), TCEP (1 mM), TBTA (100 µM) and m-phenylenediamine (40 mM) were added and the reaction was allowed to proceed for 15 h. LC-MS analysis of the sample showed >90% conversion of click reaction and >99% of oxime ligation on the protein. A gradient of 0-100% solvent A (H2O, 0.1% HCO2H) to B (CH3CN, 0.1% HCO2H) in 25 min was used for the LC-MS analysis.

Example 14

Modification of Bifunctionalized GFP 4 with Azido-TAMRA (S11) and Aminooxy-PEG (S12)

Azido-TAMRA (S11) (7 µL of 2.2 mM solution in DMSO) and aminooxy-PEG (S12) (3 kDa, from Quanta BioDesign Ltd.) (2 µL of 30 mM solution in DMSO) were added to 100 µL 4 (stock solution of 40 µM in PB). CuSO4 (1 mM), TCEP (1 mM), TBTA (100 µM) and m-phenylenediamine (40 mM) were added and the reaction was allowed to proceed for 15 h. SDS-PAGE analysis of the reaction revealed highly selective and almost complete (>95%) conversions for both oxime and click reactions.

Example 15

Prenylation of CNTF-CVIA (SEQ ID NO: 1) (5) with compound 1

Enzymatic reaction mixtures (20 mL) contained Tris.HCl (50 mM, pH 7.5), MgCl2 (10 mM), KCl (30 mM), ZnCl2 (10 JM), DTT (5.0 mM), CNTF-CVIA (SEQ ID NO: 1) (2.4 µM)(20 µL) and PFTase (200 nM). After incubation at rt for 90 min, the reaction mixture was analyzed by LC-MS to ensure complete prenylation using the gradient conditions described above.

Example 16

TAMRA-GFP-bisMTX (6) from Simultaneous Coupling of Bifunctional-GFP (4) with Azido-bisMTX (S14) and Aminooxy-TAMRA (S15)

Aminooxy-TAMRA (S15) (7 µL of 2.2 mM solution in DMSO) and azide-bisMTX (S14) (7 µL of 10 mM solution in DMSO) were added to 100 µL 4 (stock solution of 40 µM in PB). CuSO4 (1 mM), TCEP (1 mM), TBTA (100 µM) and m-phenylenediamine (40 mM) were added to the mixture and the reaction was allowed to proceed for 15 h. LC-MS analysis of the sample using the gradient conditions described above showed >90% conversion of the click reaction and >99% of oxime ligation on the bifunctionalized-protein 4. The mixture was then purified using a NAP-5 column to remove the excess reagents.

Example 17

Self-Assembly of DHFR Proteins by TAMRA-GFP-bisMTX (6)

In order to study the self-assembly of dimeric DHFR (DD) proteins by TAMRA-GFP-bisMTX (6) an equimolar mixture of relevant dimeric DHFR protein and 6 were mixed and incubated at rt for 2 h. Next the samples were analyzed by size exclusion chromatography for the formation of higher order species using our established HP-SEC method.28 Briefly, 100 µL of the incubated sample (10 µM) was injected on to a Superdex G75 size exclusion column (10×300 mm) and eluted with P500 buffer (0.5 M NaCl, 50 mM KH2PO4, 1 mM EDTA, pH 7) at 0.5 mL/min. The elution profile was monitored at 280 nm.

Example 18

Confocal Microscopy

HPB-MLT cells (0.5×106) were treated with 6 (1 µM) for control experiments and with self-assembled nanostructures at either 4 or 37° C. for 1 h in RPMI media. Cells were then pelleted by centrifugation (400×g, 5 min). After being washed twice with PBS (phosphate buffer saline), cells were incubated on Poly-Prep slides coated with poly-L-Lysine (Sigma) at 4 or 37° C. for 30 min. Cells were then fixed with 4% paraformaldehyde solution for 10 mM and washed thrice with PBS. Finally, cells were treated with ProLong Gold Antifade reagent with DAPI (Invitrogen) and a cover slip was applied. After overnight incubation they were imaged by fluorescence confocal microscopy using an Olympus FluoView 1000 BX2 upright confocal microscope.

Example 19

Flow Cytometry

HPB-MLT cells (1×106) were treated with self-assembled nanostructures (1, 0.5 and 0.1 µM) at 4° C. for 1 h in PBS buffer (containing 0.05% BSA and 0.1% sodium azide). Cells were pelleted (400×g, 10 min), washed twice, re-suspended in the supplemented PBS and their fluorescence was analyzed with a FACS Calibur flow cytometer (BD Biosciences). For the positive control experiment, HPB-MLT cells (1×106) were incubated with 40 nM FITC labeled UCHT-1 (anti-CD3 monoclonal antibody). After 2 h of incubation, cells were washed, re-suspended and analyzed by flow cytometry. A negative control experiment was performed with self-assembled nanostructures treated with CD3 negative Daudi B lymphoma cells (1×106 cells).

Example 20

Prenylation of CNTF-CVIA (SEQ ID NO: 1) with PEG-FPP analogues

CNTF-CVIA (SEQ ID NO: 1) was prenylated with both PEG containing FPP analogues as previously described [31]. A reaction consisting of 50 mM Tris HCl (pH=7.5), 50 µM ZnCl2, 10 mM MgCl2, 20 mM KCl, 15 mM DTT, 200 µM PEG FPP analogue, 2 µM CNTF-CVIA (SEQ ID NO: 1 and 1 µM yPFTase [59] was prepared. This solution was allowed to react for 4 h at 30° C. The reaction was submitted directly for LC-MS analysis to determine CNTF prenylation. The LC-MS method used was a gradient of 0-100% solvent A (H2O, 0.1% HCO2H) to solvent B (CH3CN, 0.1% HCO2H) in 25 min.

REFERENCES (1) Bertozzi, C. R. Acc. Chem. Res. 2011, 44, 651-653.
(2) Prescher, J. A.; Bertozzi, C. R. Nat Chem Biol 2005, 1, 13-21.
(3) Mamidyala, S. K.; Finn, M. G. Chem. Soc. Rev. 2010, 39, 1252.
(4) Christman, K. L.; Broyer, R. M.; Tolstyka, Z. P.; Maynard, H. D. J. Mater. Chem. 2007, 17, 2021.
(5) Prost, L. R.; Grim, J. C.; Tonelli, M.; Kiessling, L. L. ACS Chem. Biol. 2012, 7, 1603-1608.
(6) Wang, T.; Kartika, R.; Spiegel, D. A. J. Am. Chem. Soc. 2012, 134, 8958-8967.
(7) Park, S.; Yousaf, M. N. Langmuir 2008, 24, 6201-6207.
(8) Keppler, A.; Pick, H.; Arrivoli, C.; Vogel, H.; Johnsson, K. Proc. Natl. Acad. Sci. 2004, 101, 9955-9959.
(9) Yin, J.; Liu, F.; Li, X.; Walsh, C. T. J. Am. Chem. Soc. 2004, 126, 7754-7755.
(10) Chen, I.; Ting, A. Y. Curr. Opin. Biotechnol. 2005, 16, 35-40.
(11) Discher, D. E.; Eisenberg, A. Science 2002, 297, 967-973.
(12) Kim, C. H.; Axup, J. Y.; Dubrovska, A.; Kazane, S. A.; Hutchins, B. A.; Wold, E. D.; Smider, V. V.; Schultz, P. G. J. Am. Chem. Soc. 2012, 9918-9921.

(13) Hudak, J. E.; Barfield, R. M.; de Hart, G. W.; Grob, P.; Nogales, E.; Bertozzi, C. R.; Rabuka, D. Angew. Chem., Int. Ed. 2012, 51, 4161-4165.
(14) Witte, M. D.; Cragnolini, J. J.; Dougan, S. K.; Yoder, N. C.; Popp, M. W.; Ploegh, H. L. Proc. Natl. Acad. Sci. 2012, 109, 11993-11998.
(15) Yi, L.; Sun, H.; Itzen, A.; Triola, G.; Waldmann, H.; Goody, R. S.; Wu, Y.-W. Angew. Chem. Int. Ed. Engl. 2011, 50, 8287-8290.
(16) Brustad, E. M.; Lemke, E. A.; Schultz, P. G.; Deniz, A. A. J. Am. Chem. Soc. 2008, 130, 17664-17665.
(17) Kim, J.; Seo, M.-H.; Lee, S.; Cho, K.; Yang, A.; Woo, K.; Kim, H.-S.; Park, H.-S. Anal. Chem. 2013, 85, 1468-1474.
(18) Feng, L.; Hong, S.; Rong, J.; You, Q.; Dai, P.; Huang, R.; Tan, Y.; Hong, W.; Xie, C.; Zhao, J.; Chen, X. J. Am. Chem. Soc. 2013, 135, 9244-9247.
(19) Rashidian, M.; Dozier, J. K.; Lenevich, S.; Distefano, M. D. Chem. Commun. 2010, 46, 8998.
(20) Weinrich, D.; Lin, P.-C.; Jonkheijm, P.; Nguyen, U. T. T.; Schroder, H.; Niemeyer, C. M.; Alexandrov, K.; Goody, R.; Waldmann, H. Angew. Chem. Int. Ed. 2010, 49, 1252-1257.
(21) Gauchet, C.; Labadie, G. R.; Poulter, C. D. J. Am. Chem. Soc. 2006, 128, 9274-9275.
(22) Kim, M.; Kleckley, T. S.; Wiemer, A. J.; Holstein, S. A.; Hohl, R. J.; Wiemer, D. F. J. Org. Chem. 2004, 69, 8186-8193.
(23) Rashidian, M.; Song, J. M.; Pricer, R. E.; Distefano, M. D. J. Am. Chem. Soc. 2012, 134, 8455-8467.
(24) Placzek, A. T.; Gibbs, R. A. Org. Lett. 2011, 3576-3579.
(25) Labadie, G. R.; Viswanathan, R.; Poulter, C. D. J. Org. Chem. 2007, 72, 9291-9297.
(26) Subramanian, T.; Liu, S.; Troutman, J. M.; Andres, D. A.; Spielmann, H. P. Chem Bio Chem 2008, 9, 2872-2882.
(27) Duckworth, B. P.; Xu, J.; Taton, T. A.; Guo, A.; Distefano, M. D. Bioconjugate Chem. 2006, 17, 967-974.
(28) Li, Q.; So, C. R.; Fegan, A.; Cody, V.; Sarikaya, M.; Vallera, D. A.; Wagner, C. R. J. Am. Chem. Soc. 2010, 48, 17247-17257.
(29) Sonogashira, K. J. Organomet. Chem. 2002, 653, 46-49.
(30) Pompliano, D. L.; Gomez, R. P.; Anthony, N. J. J. Am. Chem. Soc. 1992, 114, 7945-7946.
(31) Rashidian, M.; Mahmoodi, M. M.; Shah, R.; Dozier, J. K.; Wagner, C. R.; Distefano, M. D. Bioconjugate Chem. 2013, 24, 333-342.
(32) Ip, N. Y.; Yancopoulos, G. D. Annu. Rev. Neurosci. 1996, 19, 491-515.
(33) Rhee, K. D.; Yang, X.-J. Adv. Exp. Med. Biol. 2010, 664, 647-654.
(34) Wen, R.; Tao, W.; Li, Y.; Sieving, P. A. Prog Retin Eye Res 2012, 31, 136-151.
(35) Rothemund, P. W. K. Nature 2006, 440, 297-302.
(36) Pistol, C.; Dwyer, C. Nanotechnology 2007, 18, 125305.
(37) Guo, P. Nat. Nanotechnol. 2010, 5, 833-842.
(38) Ke, Y.; Lindsay, S.; Chang, Y.; Liu, Y.; Yan, H. Science 2008, 319, 180-183.
(39) Matsuura, K.; Watanabe, K.; Matsuzaki, T.; Sakurai, K.; Kimizuka, N. Angew. Chem. Int. Ed. 2010, 49, 9662-9665.
(40) Salgado, E. N.; Radford, R. J.; Tezcan, F. A. Acc. Chem. Res. 2010, 43, 661-672.
(41) Hu, M.; Qian, L.; Briñas, R. P.; Lymar, E. S.; Hainfeld, J. F. Angew. Chem. Int. Ed. Engl. 2007, 46, 5111-5114.
(42) Chen, G.; Jiang, M. Chem. Soc. Rev. 2011, 40, 2254.
(43) Uhlenheuer, D. A.; Petkau, K.; Brunsveld, L. Chem. Soc. Rev. 2010, 39, 2817.
(44) Lai, J. R.; Fischbach, M. A.; Liu, D. R.; Walsh, C. T. J. Am. Chem. Soc. 2006, 128, 11002-11003.
(45) Fegan, A.; White, B.; Carlson, J. C. T.; Wagner, C. R. Chem. Rev. 2010, 110, 3315-3336.
(46) Carlson, J. C. T.; Jena, S. S.; Flenniken, M.; Chou, T.; Siegel, R. A.; Wagner, C. R. J. Am. Chem. Soc. 2006, 128, 7630-7638.
(47) Li, Q.; Hapka, D.; Chen, H.; Vallera, D. A.; Wagner, C. R. Angew. Chem. Int. Ed. 2008, 47, 10179-10182.
(48) Fegan, A.; Kumarapperuma, S. C.; Wagner, C. R. Mol. Pharm. 2012, 9, 3218-3227.
(49) Gangar, A.; Fegan, A.; Kumarapperuma, S. C.; Wagner, C. R. J. Am. Chem. Soc. 2012, 134, 2895-2897.
(50) I. Gaon, T. C. Turek, V. A. Weller, R. L. Edelstein, S. K. Singh, M. D. Distefano, J. Org. Chem. 1996, 61, 7738-7745.
(51) K. G. Zbinden, U. Obst-Sander, K. Hilpert, H. Kane, D. W. Banner, H.-J. Bohm, M. Stahl, J. Ackermann, L. Alig, L. Weber, et al., Bioorg. Med. Chem. Lett. 2005, 15, 5344-5352.
(52) M. von Delius, E. M. Geertsema, D. A. Leigh, Nat Chem 2010, 2, 96-101.
(53) I. Gaon, T. Turek, M. Distefano, Tetrahedron Lett. 1996, 37, 8833-8836.
(54) Rashidian, M.; Song, J. M.; Pricer, R. E.; Distefano, M. D. J. Am. Chem. Soc. 2012, 134, 8455-8467.
(55) A. V. Yakhnin, L. M. Vinokurov, A. K. Surin, Y. B. Alakhov, Protein Expres. Pur. 1998, 14, 382-386.
(56) B. P. Duckworth, J. Xu, T. A. Taton, A. Guo, M. D. Distefano, Bioconjugate Chem. 2006, 17, 967-974.
(57) A. Fegan, S. C. Kumarapperuma, C. R. Wagner, Molecular Pharmaceutics 2012, 9, 3218-3227.
(58) E. M. Sletten, C. R. Bertozzi Angew Chem Int Ed Engl. 2009; 48(38): 6971 6998.
(50) J. K. Dozier, M. D. Distefano, Anal. Biochem. 2012, 421, 158-163.

We claim:

1. A compound of formula I or a salt thereof:

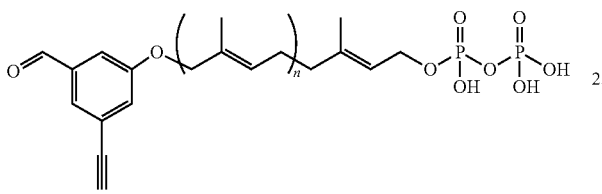

I wherein n is an integer from 1 to 2.

2. A compound of formula II or a salt thereof:

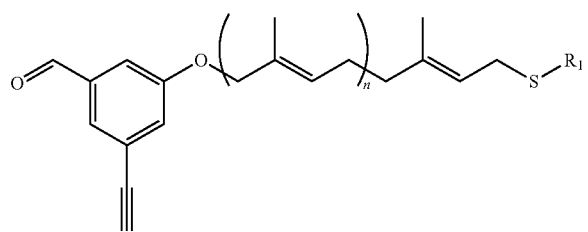

II wherein n is an integer from 1 to 2; and $R_1$ is a protein containing a CaaX motif which is attached the cysteine residue of said CaaX motif.

3. The compound of claim 2, wherein the CaaX motif is the amino acid sequence CVIA (SEQ ID NO: 1).

4. The compound of claim 2, wherein $R_1$ is Ciliary Neurotrophic Factor.

5. A compound of formula III or a salt thereof:

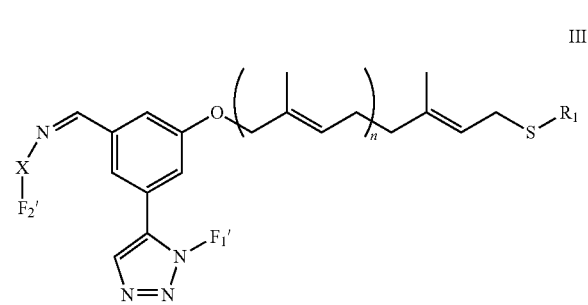

III wherein:

n is an integer from 1 to 2;

$R_1$ is a protein containing a CaaX motif which is attached the cysteine residue of said CaaX motif;

X is O or NH;

$F_1'$ is a first functional group; and $F_2'$ is a second functional group.

6. The compound of claim 5, wherein the CaaX motif is CVIA (SEQ ID NO: 1).

7. The compound of claim 5, wherein X is O.

8. The compound of claim 5, wherein X is NH.

9. The compound of claim 5, wherein $F_1'$ is a first functional group formed from reacting a compound of formula II with a compound $F_1$ containing an azide group that reacts with the ethynyl group of the compound of formula II to form a triazole linkage thereto.

10. The compound of claim 5, wherein $F_2'$ is a second functional group formed from reacting a compound of formula II with a compound F2 containing an aminooxy group that reacts with the formyl group of the compound of formula II to form an oxime linkage thereto.

11. The compound of claim 5, wherein $F_2'$ is a second functional group formed from reacting a compound of formula II with a compound F2 containing an hydrazinyl group that reacts with the formyl group of the compound of formula II to form a hydrazone linkage thereto.

12. A method of functionalizing a protein having a CaaX motif, comprising:

(a) reacting said protein with a compound of formula I or a salt thereof in the presence of a protein farnesyltransferase or a geranyl-geranyltransferase I to produce a compound of formula II or a salt thereof:

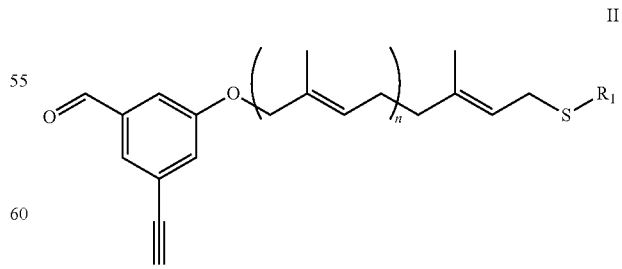

II wherein n is an integer from 1 to 2; and $R_1$ is said protein which is attached to the remainder of the compound at the cysteine residue of the CaaX motif; and (b) reacting the compound of formula II or a salt thereof with a first functional compound F₁ containing an azide group that reacts with the ethynyl group of the compound of formula II to form a triazole linkage thereto, and a second functional compound F₂ containing a reactive aminooxy or hydrazine group that reacts with the formyl group of the compound of formula II to form an oxime or hydrazone linkage thereto, thereby forming a compound of formula III or a salt thereof:

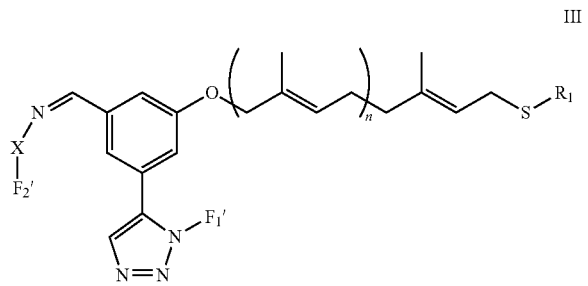

III wherein
X is O or NH;
F₁' is a first functional group; and
F₂' is a second functional group.

13. The method of claim 12, wherein n is 1.

14. The method of claim 13, wherein the compound of formula I is reacted with said protein in the presence of protein farnesyltransferase.

15. The method of claim 12, wherein n is 2.

16. The method of claim 15, wherein the compound of formula I or a salt thereof is reacted with said protein in the presence of geranylgeranyltransferase I.

17. The method of claim 12, wherein the CaaX is CVIA (SEQ ID NO: 1).

18. The method of claim 12, wherein R₁ is Ciliary Neurotrophic Factor.

19. The method of claim 12, wherein the first functional compound F₁ is azido-TAMRA fluorophore.

20. The method of claim 12, wherein the first functional compound F₁ is azido-bis-methotrexate.

21. The method of claim 12, wherein the second functional compound F₂ is aminooxy-PEG.

22. The method of claim 12, wherein the second functional compound F₂ is aminooxy-TAMRA.

23. The method of claim 12, wherein the first and second functional compounds F₁ and F₂ are reacted with the compound of formula II simultaneously.

24. A pharmaceutical composition comprising a compound of formula III or a salt thereof as described in claim 12 and a pharmaceutically acceptable carrier.

25. A method of functionalizing a protein having a CaaX motif, comprising:
a) reacting said protein with a compound of formula I or a salt thereof:

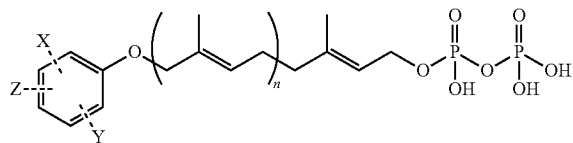

I wherein X and Y are bioorthogonal groups that are identical or different which are capable of conjugating to a functional compound; Z is H, OH, halogen or haloalkyl; and n is an integer from 1 to 2; in the presence of a protein farnesyltransferase or a geranylgeranyltransferase I to produce a compound of formula II or a salt thereof:

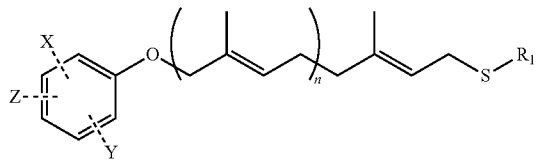

II wherein
X and Y are bioorthogonal groups that are identical or different which are capable of conjugating to a functional compound; Z is H, OH, halogen or haloalkyl; and n is an integer from 1 to 2; and R₁ is said protein which is attached to the remainder of the compound at the cysteine residue of the CaaX motif; and (b) reacting the compound of formula II or a salt thereof with a first functional compound containing a reactive group that reacts with X to form a linkage to said first functional compound, and a second functional compound containing a reactive group that reacts with Y to form a linkage to said second functional compound, thereby forming a compound of formula III or a salt thereof:

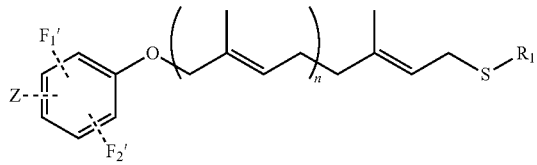

III wherein
F₁' is a first functional group; and F₂' is a second functional group.

* * * * *